US012704510B2

(12) United States Patent
Mehra et al.

(10) Patent No.: US 12,704,510 B2
(45) **Date of Patent: *Aug. 11, 2026**

(54) SIGNAL AMPLIFICATION IN PLASMONIC SPECIFIC-BINDING PARTNER ASSAYS

(71) Applicant: ZOETIS SERVICES LLC, Parsippany, NJ (US)

(72) Inventors: Rajesh K. Mehra, Parsippany, NJ (US); Vincent Chiang, Parsippany, NJ (US); Kenneth P. Aron, Parsippany, NJ (US); Asher Krell, Parsippany, NJ (US)

(73) Assignee: Zoetis Services LLC, Parsippany, NJ (US)

( * ) Notice: Subject to any disclaimer, the term of this patent is extended or adjusted under 35 U.S.C. 154(b) by 971 days.

This patent is subject to a terminal disclaimer.

(21) Appl. No.: 17/527,256

(22) Filed: Nov. 16, 2021

(65) Prior Publication Data

US 2022/0074934 A1 Mar. 10, 2022

Related U.S. Application Data

(60) Continuation of application No. 16/654,988, filed on Oct. 16, 2019, now Pat. No. 11,209,430, which is a (Continued)

(51) Int. Cl.
*B82Y 15/00* (2011.01)
*G01N 33/553* (2006.01)

(52) U.S. Cl.
CPC ............ *G01N 33/553* (2013.01); *B82Y 15/00* (2013.01)

(58) Field of Classification Search
None
See application file for complete search history.

(56) References Cited

U.S. PATENT DOCUMENTS 4,704,366 A 11/1987 Juarez-Salinas et al.
5,061,381 A 10/1991 Burd
(Continued)

FOREIGN PATENT DOCUMENTS

CN 1417586 A 5/2003
CN 1798976 A 7/2006
(Continued)

OTHER PUBLICATIONS

Kengo Yamaguchi, "Construction of high-density aggregates composed of various metal nanoparticles and their surface-enhanced Raman scattering properties", Proceedings of the Spring Annual Meeting of the Chemical Society of Japan, Mar. 10, 2016. vol. 96th, p. RMBUNNO.3PC-239. 1 page.
(Continued)

*Primary Examiner* — Rebecca M Giere
(74) *Attorney, Agent, or Firm* — Prakash Subbiah

(57) ABSTRACT

The present invention relates to analyte detection devices and methods of using such devices to detect minute quantities of a target analyte in a sample. In particular, the invention provides an analyte detection device comprising a plurality of composite metallic nanostructures conjugated to analyte binding partners and a surface containing a metallic nanolayer on which a plurality of capture molecules is immobilized. Methods of preparing composite nanostructures are also described.

31 Claims, 7 Drawing Sheets

Related U.S. Application Data division of application No. 14/825,668, filed on Aug. 13, 2015, now Pat. No. 10,488,409.

(60) Provisional application No. 62/037,071, filed on Aug. 13, 2014, provisional application No. 62/082,468, filed on Nov. 20, 2014.

(56) References Cited

U.S. PATENT DOCUMENTS 5,122,284 A 6/1992 Braynin et al.
5,186,844 A 2/1993 Burd et al.
5,304,348 A 4/1994 Burd et al.
5,457,053 A 10/1995 Burd et al.
5,624,597 A 4/1997 Buhl et al.
5,693,233 A 12/1997 Schembri
5,939,021 A 8/1999 Hansen et al.
6,579,726 B1 6/2003 Natan et al.
6,660,381 B2 12/2003 Halas et al.
6,685,986 B2 2/2004 Oldenburg et al.
6,699,724 B1 3/2004 West et al.
6,861,263 B2 3/2005 Natan
6,970,239 B2 11/2005 Chan et al.
7,135,054 B2 11/2006 Jin et al.
7,144,627 B2 12/2006 Halas et al.
7,212,692 B2 5/2007 Yan
7,307,731 B2 12/2007 Naya
7,405,054 B1 7/2008 Hasenbank et al.
7,648,595 B2 1/2010 Jin et al.
7,732,145 B2 6/2010 Kang et al.
7,790,066 B2 9/2010 Wang et al.
7,807,633 B2 10/2010 Haynie
8,101,424 B2 1/2012 Geddes
8,110,250 B2 2/2012 Ojima et al.
8,263,418 B2 9/2012 Brennan et al.
8,426,152 B2 4/2013 Gerion et al.
8,597,897 B2 12/2013 Kim et al.
8,628,727 B2 1/2014 Van Duyne et al.
8,697,129 B2 4/2014 Qian et al.
8,753,559 B2 6/2014 Yang et al.
8,784,895 B2 7/2014 Messersmith et al.
8,808,420 B2 8/2014 Aherne et al.
9,034,656 B2 5/2015 Mehra et al.
9,040,310 B2 5/2015 Ashworth-Sharpe et al.
9,217,746 B2 12/2015 Geddes
9,308,582 B2 4/2016 Sun et al.
9,835,622 B2 12/2017 Mehra et al.
9,921,218 B2 3/2018 Mehra et al.
10,281,465 B2 5/2019 Mehra et al.
10,429,383 B2 10/2019 Mehra et al.
10,488,409 B2 11/2019 Mehra et al.
11,209,430 B2 12/2021 Mehra et al.
11,215,614 B2 1/2022 Mehra et al.
11,255,854 B2 2/2022 Mehra et al.
11,614,447 B2 3/2023 Mehra et al.
11,977,072 B2 5/2024 Mehra et al.
2001/0002315 A1 5/2001 Schultz et al.
2002/0177143 A1* 11/2002 Mirkin ..................... B22F 1/10 436/526
2003/0170618 A1 9/2003 Chien et al.
2005/0037437 A1 2/2005 Zeidler
2006/0240573 A1 10/2006 Kao et al.
2006/0246513 A1 11/2006 Bohannon
2007/0054337 A1 3/2007 Ferning et al.
2007/0092978 A1 4/2007 Mink et al.
2008/0213814 A1 9/2008 Gerion et al.
2008/0227219 A1 9/2008 Gamez
2009/0018025 A1 1/2009 Shao et al.
2010/0028410 A1 2/2010 Haynie
2010/0062545 A1 3/2010 Geddes
2010/0120057 A1 5/2010 Mehra et al.
2010/0136566 A1 6/2010 Mehra et al.
2010/0159441 A1 6/2010 Chiang et al.
2010/0184086 A1 7/2010 Callister
2011/0065088 A1 3/2011 Kang et al.
2011/0124125 A1 5/2011 Mehra et al.
2011/0136143 A1 6/2011 Castro et al.
2011/0136155 A1 6/2011 Mehra et al.
2011/0275061 A1 11/2011 Weidemaier et al.
2012/0101007 A1 4/2012 Ahern et al.
2012/0162640 A1 6/2012 Sakagami
2012/0208174 A1 8/2012 Galush et al.
2012/0219966 A1 8/2012 Kawamura
2012/0252005 A1 10/2012 Chiang et al.
2013/0034854 A1 2/2013 Ashworth-Sharpe et al.
2013/0115634 A1 5/2013 Mehra et al.
2013/0130404 A1 5/2013 Mehra et al.
2013/0172207 A1 7/2013 Dai et al.
2013/0189793 A1 7/2013 Qian et al.
2013/0203075 A1 8/2013 Svenson et al.
2013/0230717 A1 9/2013 Xia et al.
2013/0252275 A1 9/2013 Tokonami et al.
2014/0105982 A1 4/2014 Oldenburg et al.
2014/0121125 A1 5/2014 Mehra et al.
2014/0162067 A1 6/2014 Shahjamali et al.
2014/0170070 A1 6/2014 Qian et al.
2014/0272932 A1 9/2014 Muerhoff et al.
2014/0272933 A1 9/2014 Dawson et al.
2014/0308756 A1 10/2014 Gautier et al.
2014/0349317 A1 11/2014 Kobayashi
2015/0004102 A1 1/2015 Salman et al.
2015/0017258 A1 1/2015 Azzazy et al.
2015/0038355 A1 2/2015 Tan et al.
2015/0212005 A1 7/2015 Akhavan-Tafti et al.
2015/0247846 A1 9/2015 Gerion et al.
2015/0293088 A1 10/2015 Mehra et al.
2016/0047804 A1 2/2016 Mehra et al.
2016/0120978 A1 5/2016 Guler et al.
2016/0153972 A1 6/2016 Daynes et al.
2016/0202251 A1 7/2016 Goh et al.
2017/0038366 A1 2/2017 Mehra et al.
2018/0059104 A1 3/2018 Mehra et al.
2018/0156790 A1 6/2018 Mehra et al.
2019/0219572 A1 7/2019 Mehra et al.
2020/0110086 A1 4/2020 Mehra et al.
2022/0082562 A1 3/2022 Mehra et al.
2022/0091113 A1 3/2022 Mehra et al.
2023/0333102 A1 10/2023 Mehra et al.

FOREIGN PATENT DOCUMENTS

CN 1902496 A 1/2007
CN 101490554 A 7/2009
CN 102023151 A 4/2011
CN 102103145 A 6/2011
CN 102323422 A 1/2012
CN 103335984 A 10/2013
CN 104105965 B 7/2016
CN 106290893 A 1/2017
JP H03164195 A 7/1991
JP H07501880 A 2/1995
JP H10132818 A 5/1998
JP 2000028612 A 1/2000
JP 2000028614 A 1/2000
JP 2000146959 A 5/2000
JP 2001513198 A 8/2001
JP 2003514224 A 4/2003
JP 2003149244 A 5/2003
JP 2005195440 A 7/2005
JP 2005520125 A 7/2005
JP 2007114129 A 5/2007
JP 2008524602 A 7/2008
JP 2008527332 A 7/2008
JP 2009516199 A 4/2009
JP 2009150708 A 7/2009
JP 2010286331 A 12/2010
JP 2010537155 A 12/2010
JP 2011525966 A 9/2011
JP 2012132875 A 7/2012
JP 2012215472 A 11/2012
JP 2013525800 A 6/2013
JP 2014228385 A 12/2014
JP 20157652 A 1/2015
JP 2015507078 A 3/2015

(56) References Cited

FOREIGN PATENT DOCUMENTS

| | | | |
|---|---|---|---|
| JP | 2015509936 | A | 4/2015 |
| JP | 2015102337 | A | 6/2015 |
| JP | 2016510126 | A | 4/2016 |
| TW | 201408690 | A | 3/2014 |
| WO | WO-0109388 | A1 | 2/2001 |
| WO | WO-03008539 | A2 | 1/2003 |
| WO | WO-2006074076 | A1 | 7/2006 |
| WO | WO-2007047924 | A2 | 4/2007 |
| WO | WO-2007053201 | A2 | 5/2007 |
| WO | WO-2007061793 | A2 | 5/2007 |
| WO | WO-2008086054 | A2 | 7/2008 |
| WO | WO-2008116093 | A2 | 9/2008 |
| WO | WO-2009117510 | A2 | 12/2009 |
| WO | WO-2010006201 | A2 | 1/2010 |
| WO | WO-2011095636 | A1 | 8/2011 |
| WO | WO-2011063003 | A2 | 9/2011 |
| WO | WO-2011063235 | A2 | 10/2011 |
| WO | WO-2011139792 | A2 | 11/2011 |
| WO | WO-2011148870 | A1 | 12/2011 |
| WO | WO-2012077756 | A1 | 6/2012 |
| WO | WO-2013067524 | A1 | 5/2013 |
| WO | WO-2013078227 | A1 | 5/2013 |
| WO | WO-2013169640 | A1 | 11/2013 |
| WO | WO-2014020293 | A1 | 2/2014 |
| WO | WO-2014059274 | A1 | 4/2014 |
| WO | WO-2014132833 | A1 | 9/2014 |
| WO | WO-2015160923 | A1 | 10/2015 |
| WO | WO-2016007942 | A1 | 1/2016 |
| WO | WO-2016134214 | A1 | 8/2016 |
| WO | WO-2016025703 | A2 | 9/2016 |
| WO | WO-2016170183 | A1 | 10/2016 |
| WO | WO-2017024163 | A1 | 2/2017 |
| WO | WO-2018140953 | A1 | 8/2018 |

OTHER PUBLICATIONS

Kooij E.S., "From nanorods to nanostars: Turning the optical properties of gold nanoparticles", Colloids and Surfaces A: Physicochem. Eng. Aspects, 2012, vol. 413, pp. 231-238.

[Author Unknown], Alpha Assays Protein: Protein Interaction User Guide, PerkinElmer, Waltham, MA, USA, May 2011, 40 pages, https://www.blossombio.com/pdf/products/UG_Alphatech.pdf.

Shkilnyy, A. et al., "Poly(ethylene glycol)-stabilized silver nanoparticles for bioanalytical applications of SERS spectroscopy", Analyst (Jan. 1, 2009); vol. 134, No. 9, p. 1868-1872. Epub Jul. 6, 2009.

Atanasov, P.A. et al., "Noble metallic nanostructures: preparation, properties, applications", Journal of Physics: Conference Series 514 (2014), pp. 1-8.

[Author Unknown], Alpha Protein-Protein Interaction User Guide, PerkinElmer Japan, Nov. 2017, 40 pages, https://www.perkinelmer.co.jp/Portals/0/resource/tech/tech_Is/protocol_collection/Alpha_Protein-Protein_Interaction_userguide.pdf.

[Author Unknown], "Sorvall Legend XT Sorvall Legend XTR Instruction Manual," Thermo Fisher Scientific, No. 50119927-4, Feb. 14, 2011 (Feb. 14, 2011), pp. 1-59. Retrieved from the Internet: http://core.phmtox.msu.edu/Scheduling/ItemDocs/40/XTR_Manual.pdf on Mar. 7, 2018 (Mar. 7, 2018).

Bangs Laboratories, Inc., "Lateral Flow Tests," TechNote 303, available at http://www.bangslabs.com/sites/default/files/bangs/docs/pdf/303.pdf, 1999. 6 pages.

Bolduc and Masson, "Advances in surface plasmon resonance sensing with nanoparticles and thin films: nanomaterials, surface chemistry, and hybrid plasmonic techniques." Anal Chem. (2011); 83 (21): 8057-8062. Epub Aug. 29, 2011.

Bui, et al., "Gold Nanoparticle Aggregation-Based Highly Sensitive DNA Detection Using Atomic Force Microscopy," Anal. Bioanal. Chem., vol. 388: 1185-1190, 2007.

Cui, et al., "Synthesis of AgcoreAushell Bimetallic Nanoparticles for Immunoassay Based on Surface-Enhanced Raman Spectroscopy". J Phys Chem B. (Mar. 9, 2006); 110(9): 4002-4006.

Dong, P., et al., "Ultrathin Gold-Shell Coated Silver Nanoparticles onto a Glass Platform for Improvement of Plasmonic Sensors." ACS Appl. Mater. Interfaces (2013); 5 (7): 2392-2399.

European Patent Application No. 12852350.3, Extended European Search Report dated May 13, 2015, 10 pages.

European Patent Application No. 15831667.9, Supplementary European Search Report dated Nov. 30, 2017, 9 pages.

European Patent Application No. 16833889.5, Extended European Search Report dated Dec. 21, 2018, 7 pages.

European Patent Application No. 18196372.9, Extended European Search Report dated Feb. 21, 2019, 13 pages.

European Patent Application No. 18745189.3, Extended Supplementary European Search Report dated Dec. 2, 2020, 16 pages.

European Patent Application No. 18745189.3, Partial Supplementary European Search Report dated Aug. 27, 2020, 20 pages.

European Patent Application No. 21177342.9, Extended European Search Report dated Dec. 23, 2021, 15 pages.

Fan, Chao-Ming et al. "A study of double antigen sandwich colloidal gold immunochromatography rapid detection for *Mycobacterium tuberculosis* antibody", US National Library of Medicine Database accession No. NLM21729624 (May 2011), 2 pages.

Gupta, S. et al., "Characterization and optimization of gold nanoparticle-based silver-enhanced immunoassays", Anal. Chem. (2007), 79: 3810-3820.

Gupta, R. et al., "Preparation and characterization of surface plasmon resonance tunable gold and silver films", Journal of Applied Physics (2002), 92(9): 5264-5271.

Haes, A., et al., "Nanoscale plasmonics begins to unravel Alzheimer's disease", LaserFocusWorld, Jun. 1, 2005, www.laserfocusworld.com/test-measurement/research/article/16555980/nanoscale-plasmonics-begins-to-unravel-alzheimers-disease#:~: text=Nanoscale%20plasmonics%20begins%20to%20unravel%20Alzheimer%E2%80%99s%20disease%20An,an%20Alzheimer%E2%80%99s%20clinical%20diagnostic%20test.%20Jun%201st%2C%202005, 10 pages.

Helmerhorst, E. et al., "Real-time and label-free bio-sensing of molecular interactions by surface plasmon resonance: A Laboratory Medicine Perspective", Clin Biochem Rev (2012), 33: 161-173.

Hong, W. et al. "Development of an up-converting phosphor technology-based 10-channel lateral flow assay for profiling antibodies against Yersinia pestis", J Microbiol Methods (2010), 83(2): 133-140.

Howes, et al., "Bionanotechnology. Colloidal nanoparticles as advanced biological sensors". Science (Oct. 3, 2014); 346(6205): 1247390. Epub Oct. 2, 2014.

Jana D., et al., "Capping Agent-Free Gold Nanostars Show Greatly Increased Versatility and Sensitivity for Biosensing," Analytical Chemistry, 2015, vol. 87(7), pp. 3964-3972.

Jana, et al., Supporting Information for "Capping Agent-Free Gold Nanostars Show Greatly Increased Versatility and Sensitivity for Biosensing". Anal. Chem. (2015); 87(7): 3964-3972, 11 pages.

Jia, K., et al., "Strong Improvements of Localized Surface Plasmon Resonance Sensitivity by Using Au/Ag Bimetallic Nanostructures Modified with Polydopamine Films." ACS Appl. Mater. Interfaces (2014); 6 (1): 219-227.

Kvtek, O., et al., "Noble metal nanostructures influence of structure and environment on their optical properties." Journal of Nanomaterials (2013); vol. 2013, Article ID 743684, pp. 1-15, 16 pages.

LamdaGen. Plasmonic ELSA. [online] Apr. 21, 2014 [retrieved Nov. 27, 2015]. Available on the internet at URL:http://web.archive.org/web/20140421112507/http://lamdagen.com/lspr-verview/plasmonic-elisa/, 1 page.

Li, M. et al., "Three-dimensional hierarchical plasmonic nano-architecture enhanced surface-enhanced raman scattering immunosensor for cancer biomarker detection in blood plasma", ACS Nano. (2013), 7(6): 4967-4976.

Lyon, et al., "Colloidal Au-Enhanced Surface Plasmon Resonance Immunosensing". Anal. Chem. (1998); 70: 5177-5183.

Mohammed and Desmulliez, "Lab-on-a-chip based immunosensor principles and technologies for the detection of cardiac biomarkers: A Review", Lab Chip (2011), 11(4): 569-595.

(56) References Cited

OTHER PUBLICATIONS

Moreton, et al., "Functionalization of Hollow Gold Nanospheres for use as Stable, Red-shifted SERS Nanotags". The Royal Society of Chemistry (2013); 7(14): 6075-6082, 8 pages, published on Mar. 6, 2015.
Mott, et al., "A Study on the Plasmonic Properties of Silver Core Gold Shell Nanoparticles: Optical Assessment of the Particle Structure". Japanese Journal of Applied Physics (Jun. 20, 2011); vol. 50, No. 6R, 8 pages.
Mott, et al., "Synthesis of Size and Shape Controlled Silver Nanoparticles Coated by a Thin Layer of Gold and Their Use as Ultrasensitive Biomolecular Probes." Mater. Res. Soc. Symp. Proc. (2010); Materials Research Society 1253-K09-04, vol. 1253, 6 pages.
Murshid, et al., "Gold plating of silver nanoparticles for superior stability and preserved plasmonic and sensing properties". Chem Commun. (Dec. 18, 2013); 49(97):11355-11357.
Nitin, et al., "Oligonucleotide-Coated Metallic Nanoparticles as a Flexible Platform for Molecular Imaging Agents," Bioconjug. Chem. (2007); vol. 18(6): 2090-2096.
Oh, Bo-Ram et al., "Integrated nanoplasmonic sensing for cellular functional immunoanalysis using human blood", ACS Nano. (2014), 8(3): 2667-2676.
Park, et al., "Nanostar Clustering Improves the Sensitivity of Plasmonic Assays". Bioconjug Chem. (Aug. 19, 2015); 26(8): 1470-1474. Epub Jul. 2, 2015.
Paul, S. et al., "Surface plasmon resonance imaging detection of silver nanoparticle-tagged immunoglobulin", J. R. Soc. Interface (2011), 8: 1204-1211.
PCT/US2012/066108, International Preliminary Report on Patentability, mailed May 27, 2014, 7 pages.
PCT/US2012/066108, International Search Report and Written Opinion, mailed Mar. 25, 2013, 10 pages.
PCT/US2012/066108, Invitation to Pay Additional Fees, mailed Jan. 8, 2013, 2 pages.
PCT/US2015/045041, International Preliminary Report on Patentability, dated Feb. 14, 2017, 8 pages.
PCT/US2015/045041, International Search Report and Written Opinion, mailed Jul. 26, 2016, 13 pages.
PCT/US2015/045041, Invitation to Pay Additional Fees, mailed Oct. 20, 2015, 3 pages.
PCT/US2016/045606, International Preliminary Report on Patentability, dated Feb. 6, 2018, 9 pages.
PCT/US2016/045606, International Search Report, mailed on Oct. 24, 2016, 2 pages.
PCT/US2016/045606, Written Opinion, mailed on Oct. 24, 2016, 8 pages.
PCT/US2018/015981, International Preliminary Report on Patentability, dated Jul. 30, 2019, 15 pages.
PCT/US2018/015981, International Search Report and Written Opinion, mailed Apr. 13, 2018, 22 pages.
Pei et al., "Highly sensitive SERS-based immunoassay with simultaneous utilization of self-assembled substrates of gold nanostars and aggregates of gold nanostar". Journal of Materials Chemistry B (2013); 1(32): 3992-3998.
Raphael, M.P. et al., "Quantitative LSPR imaging for biosensing with single nanostructure resolution", Biophysical Journal (2013), 104(1): 30-36.
Riskin, et al., "Ultrasensitive Surface Plasmon Resonance Detection of Trinitrotoluene by a Bis-aniline-Cross-Linked Au Nanoparticles Composite". JACS (2009); 131: 7368-7378.
Ruemmele, J.A. et al., "A localized surface plasmon resonance imaging instrument for multiplexed biosensing", Anal Chem. (2013), 85(9): 4560-4566.
Seekell, K. et al., "Optimization of immunolabeled plasmonic nanoparticles for cell surface receptor analysis", Methods. (2012), 56(2): 310-316.
Shao, Y. et al., "Optical fiber LSPR biosensor prepared by gold nanoparticle assembly on polyelectrolyte multilayer", Sensors (2010), 10: 3585-3596.
Singh, et al., "Intensification of surface enhanced Raman scattering of thiol-containing molecules using Ag@Au core@shell nanoparticles". Journal of Applied Physics (2011); 109 (9): 1-38, 094301. Epub May 2, 2011.
Song, et al., "Gold-modified silver nanorod arrays for SERS-based immunoassays with improved sensitivity", Journals of Materials Chemistry B (Nov. 1, 2014); 2(43): 7488-7494.
Sotiriou, et al., "Plasmonic biocompatible silver-gold alloyed nanoparticles", Chem Commun (Camb). (Nov. 14, 2014); 50(88): 13559-13562.
Stringer et al., "Development of an optical biosensor using gold nanoparticles and quantum dots for the detection of Porcine Reproductive and Respiratory Syndrome Virus", Sensors and Actuators B: Chemical (2008), 134(2): 427-431.
Tauran, Y. et al., "Molecular recognition by gold, silver and copper nanoparticles", World J Biol Chem. (2013), 4(3): 35-63.
Tokel, O. et al., "Advances in plasmonic technologies for point of care applications", Chem Rev. (2014), 114(11): 5728-5752.
Truong, P.L., et al., "A new method for non-labeling attomolar detection of diseases based on an individual gold nanorod immunosensor." Lab Chip (2011); 11: 2591-2597.
Walters and Parkin, "The incorporation of noble metal nanoparticles into host matrix thin films: synthesis, characterisation and applications", J. Mater. Chem. (2009), 19: 574-590.
Wu, et al., "Bioassay of prostate-specific antigen (PSA) using microcantilevers." Nature Biotechnology (2001); 19: 856-860.
Wu et al., "Gold Nanoparticle-Based Enzyme-Linked Antibody-Aptamer Sandwich Assay for Detection of *Salmonella typhimurium*." ACS Applied Materials and Interfaces (2014); 6: 16974-16981.
Zhang and Cremer, "Interactions between macromolecules and ions: the Hofmeister series." Blood (2006); 10 (6): 658-663.
Zheng, et al., "[Gold Nanoparticles-Based Localized Surface Plasmon Resonance Scattering Analysis Method for the Determination of Trace Amounts of Hg(II)]". Spectroscopy and Spectral Analysis (Jun. 2014); 34(6): 1477-1481.
Final Office Action for U.S. Appl. No. 13/682,306, dated Dec. 10, 2014, 13 Pages.
Non Final Office Action for U.S. Appl. No. 13/682,306, dated Sep. 6, 2013, 22 Pages.
Search Report for Chinese Application No. 201280057143.5, dated Apr. 29, 2015, 8 Pages.

* cited by examiner

| ng/ml | peak_shift pm |
|---|---|
| 0 | 18.96 |
| 1 | 43.05 |
| 10 | 56.31 |
| 100 | 279.04 |

Blue= PBS; green= 1 ng/ml CRP; red= 10 ng/ml CRP and pink= 100 ng/ml CRP

Calibration Curve for Assay Time of 700 s

| ng/ml | 15-20 min incubation peak_shift pm | No wash/incubation peak_shift pm | |
|---|---|---|---|
| 0 | 18.96 | 14.06 | |
| 1 | 43.05 | | |
| 10 | 56.31 | 43.38 | 6.66 |
| 100 | 279.04 | 137.44 | |

10 pg/mL

SIGNAL AMPLIFICATION IN PLASMONIC SPECIFIC-BINDING PARTNER ASSAYS

CROSS REFERENCE TO RELATED APPLICATIONS

This application is a continuation of U.S. patent application Ser. No. 16/654,988, filed Oct. 16, 2019, (now U.S. Pat. No. 11,209,430, issued Dec. 28, 2021), which is a divisional of U.S. patent application Ser. No. 14/825,668, filed Aug. 13, 2015 (now U.S. Pat. No. 10,488,409, issued Nov. 26, 2019), which claims the benefit of priority to U.S. Provisional Application No. 62/037,071, filed Aug. 13, 2014 and U.S. Provisional Application No. 62/082,468, filed Nov. 20, 2014, each of which is incorporated herein by reference in its entirety.

FIELD OF THE INVENTION

The present invention relates to systems and methods for detecting target analytes in a sample. In particular, the present invention provides a local plasmon resonance-based analyte detection system capable of detecting a minute quantity of a target analyte in a sample.

BACKGROUND OF THE INVENTION

Current immunoassays and biomolecule binding assays typically require multiple steps and sophisticated equipment to perform the assays. The lack of sensitivity and the complexity involved in performing such heterogeneous assays arises from the specific need to separate labeled from unlabeled specific binding partners.

Attempts to develop assays based on the local surface plasmon resonance (LSPR) properties of noble metal nanoparticles have been made (Tokel et al., Chem Rev., Vol. 114:5728-5752, 2014). LSPR is the collective oscillation of electrons in nanometer-sized structures induced by incident light. Metallic nanoparticles have a strong electromagnetic response to refractive index changes in their immediate vicinity and thus shifts in the resonance frequency of the nanoparticles can be measured as an indicator of molecules binding to the nanoparticle surface. Although metallic nanoparticles, particularly gold nanoparticles, have been employed in diagnostic assays to detect binding events, such assays generally suffer from low sensitivity and cannot be used to quantitatively monitor the kinetics of sequential binding events.

Thus, improved assay methods employing a homogenous format while providing increased sensitivity are needed. Assays utilizing standard laboratory techniques, such as spectroscopy, would also be desirable.

SUMMARY OF THE INVENTION

The present invention is based, in part, on the discovery that composite metallic nanostructures can enhance the optical signals induced by binding of a molecule to a metallic nanolayer surface. The amplification observed greatly increases the sensitivity of detecting specific biomolecular binding events such that sub-picogram quantities of the biomolecule can be detected. Accordingly, the present invention provides analyte detection devices and methods of using such devices to detect minute quantities of a target analyte in a sample.

In one embodiment, the analyte detection devices comprise a plurality of detection conjugates, a surface containing a metallic nanolayer, and a plurality of capture molecules, wherein the capture molecules are immobilized on the metallic nanolayer and are capable of specifically binding to the target analyte. In embodiments in which the analyte detection devices are configured in a sandwich assay format, the detection conjugates comprise composite metallic nanostructures coupled to binding partners that are capable of specifically binding to the target analyte. In embodiments in which the analyte detection devices are configured in a direct competitive assay format, the detection conjugates composite metallic nanostructures coupled to target analytes.

The composite metallic nanostructures in the detection conjugates generally comprise at least two noble metals, transition metals, alkali metals, lanthanides, or combinations thereof. In some embodiments, the composite metallic nanostructures comprise at least two metals selected from gold, silver, copper, platinum, palladium, cadmium, iron, nickel, and zinc. In certain embodiments, each of the composite metallic nanostructures comprises a core of a first metal and a coating of a second metal. In some embodiments, the core may be silver or copper with a gold coating. In other embodiments, the core of a first metal may be dissolved following coating such that a hollow structure comprised of the second coating metal results.

The metallic nanolayer deposited on the surface can be a metallic film or comprised of a plurality of metallic nanostructures immobilized on the surface. The metallic nanolayer can also be comprised of a noble or transition metal. In some embodiments, the metallic nanolayer comprises gold, silver, copper, platinum, palladium, cadmium, zinc or a composite thereof. In one embodiment, the metallic nanolayer comprises gold. In another embodiment, the metallic nanolayer comprises silver. In still another embodiment, the metallic nanolayer comprises a silver nanolayer overlaid with a gold nanolayer.

The present invention also provides methods of detecting a target analyte in a sample using the analyte detection devices described herein. In one embodiment, the methods comprise mixing the sample with a plurality of detection conjugates, contacting the mixture with a surface containing a metallic nanolayer on which a plurality of capture molecules are immobilized, exposing the surface to a light source at a wavelength range within the ultraviolet-visible-infrared spectrum; and measuring an optical signal from the surface, wherein a change in the optical signal indicates the presence of the target analyte in the sample. In certain embodiments, the methods of the present invention are capable of detecting femtogram to nanogram quantities of a target analyte in sample.

The present invention includes an assay complex comprising a detection conjugate comprising a composite metallic nanostructure coupled to a binding partner; a target analyte; and a metallic nanolayer-coated bead on which a capture molecule is immobilized, wherein the binding partner in the detection conjugate is bound to a first epitope on the target analyte and the capture molecule is bound to a second epitope on the target analyte, thereby forming a complex comprising the detection conjugate, target analyte, and the capture molecule. In some embodiments, the composite metallic nanostructure is a gold-coated silver nanostructure or a gold-coated copper nanostructure and the metallic nanolayer coating on the bead comprises gold.

In another aspect, the present invention provides a method for preparing composite metallic nanostructures for use in the detection devices and methods described herein. In one embodiment, the methods comprise preparing a first solution comprising a mixture of a polymer and chloroauric acid, preparing a second solution comprising silver or copper nanostructures, and incubating the first solution with the second solution for a period of time, wherein the resulting mixture comprises gold-coated silver nanostructures or gold-coated copper nanostructures. In certain embodiments, a reducing agent, such as ascorbic acid, is added to the reaction mixture to increase the quantity of nanostructures produced. In one embodiment, the polymer in the first solution is polyvinylpyrrolidone. In another embodiment, the polymer in the first solution is polyvinyl alcohol.

DETAILED DESCRIPTION OF THE INVENTION

Figure 1:
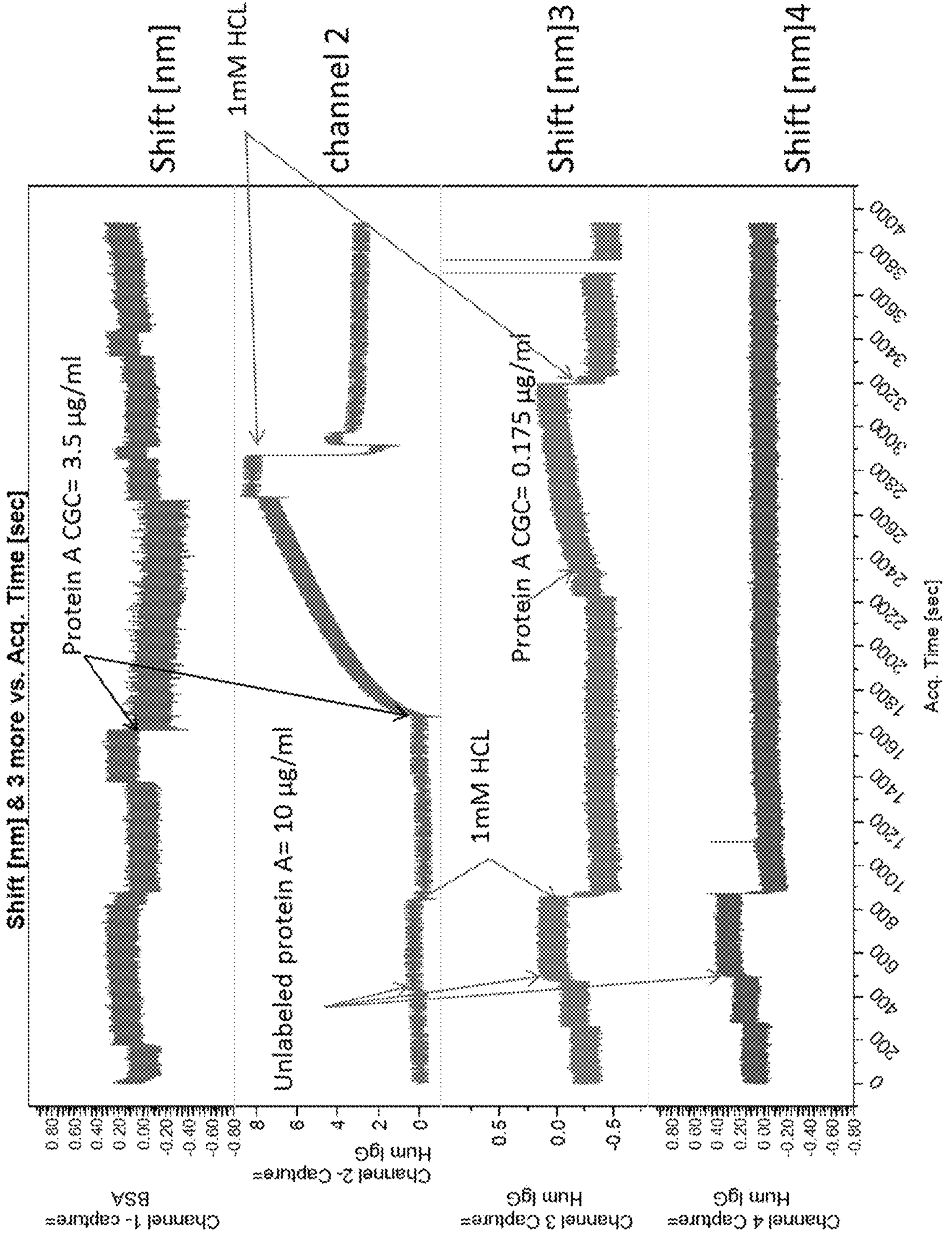
FIG. 1. Plot of shift in peak wavelength versus acquisition time for a bovine serum albumin (BSA)-coupled gold nanolayer sensor (channel 1) and human IgG-coupled gold nanolayer sensors (channels 2-4). Arrows indicate the injection sequence and concentration of unlabeled protein A, 1 mM HCl, or protein A labeled with colloidal gold (CGC).

The present invention is based, in part, on the discovery that significant amplification in LSPR-based assays can be achieved with composite metallic nanostructure-labeled binding partners. Thus, the present invention provides analyte detection devices comprising an LSPR-surface, e.g., a surface containing a metallic nanolayer, a plurality of capture molecules immobilized to the metallic nanolayer, and a plurality of detection conjugates comprising composite metallic nanostructures coupled to biomolecules.

The analyte detection devices can be configured in a sandwich assay format or a direct competitive assay format. For instance, in one embodiment, an analyte detection device in a sandwich assay format comprises (i) a plurality of detection conjugates, wherein the conjugates comprise composite metallic nanostructures coupled to binding partners that are capable of specifically binding to a target analyte, (ii) a surface containing a metallic nanolayer, and (iii) a plurality of capture molecules, wherein the capture molecules are immobilized on the metallic nanolayer and are capable of specifically binding to the target analyte. In another embodiment, an analyte detection device in a direct competitive assay format comprises (i) a plurality of detection conjugates, wherein the conjugates comprise composite metallic nanostructures coupled to target analytes, (ii) a surface containing a metallic nanolayer, and (iii) a plurality of capture molecules, wherein the capture molecules are immobilized on the metallic nanolayer and are capable of specifically binding to the target analytes.

The analyte detection devices of the invention comprise a surface containing a metallic nanolayer. The surface can be any suitable size and shape, such as a chip, a well, a cuvette, or a bead. In some embodiments, the surface is a rectangular chip. In other embodiments, the surface is a disc. In certain embodiments, the surface is the bottom, the cover, and/or interior walls of a cuvette (e.g., cylindrical or rectangular cuvette). In still other embodiments, the surface is an array of non-metallic particles. The surface can be manufactured from various materials including, but not limited to, glass, quartz, silicon, silica, polystyrene, graphite, fabric (e.g. polyethylene fabrics), mesh, or a membrane (e.g. latex, polyvinyl, nylon, or polyester membranes).

A metallic nanolayer is preferably deposited on the surface. The metallic nanolayer may, in some embodiments, cover the entire surface area of the particular surface. In other embodiments, the metallic nanolayer may be deposited only on a portion of the surface. For example, the surface may contain a plurality of depressions or wells and the metallic nanolayer is deposited within the depressions or wells. In other embodiments, the metallic nanolayer may be applied to the surface as a plurality of spaced deposits across the surface. The optical properties of the metallic nanolayer can be adjusted by varying the thickness of the nanolayer and/or the nature of nanostructures. In one embodiment, the nanolayer is comprised of metallic nanoislands. In another embodiment, the nanolayer is comprised of nanorods. Suitable thicknesses of the metallic nanolayer for use in the devices and methods of the invention include from about 0.5 nm to about 100 nm, about 5 nm to about 30 nm, or about 3 nm to about 10 nm. Exemplary surfaces with a metallic nanolayer coating that can be used in the devices and methods of the invention include the surfaces described in U.S. Patent Publication No. 2006/0240573, which is hereby incorporated by reference in its entirety.

In certain embodiments, the metallic nanolayer is a metallic film. Methods of depositing metallic films on a substrate surface are known to those of skill in the art and include, but are not limited to, atomic layer deposition, pulsed laser deposition, drop casting, vapor deposition, and adsorption. See, e.g., Atanasov et al., Journal of Physics: Conference Series 514 (2014); Walters and Parkin, Journal of Materials Chemistry, 19:574-590, 2009; and Gupta et al., J. Appl. Phys. 92, 5264-5271, 2002, each of which is herein incorporated by reference in its entirety. The metallic film may comprise other components, e.g. the metallic film may be a polymer film, a Langmuir-Blodgett film or an oxide film. In some embodiments, the metallic film comprises two layers, wherein each layer comprises a different metal. By way of example, the metallic film may comprise a silver layer overlaid with a gold layer.

In other embodiments, the metallic nanolayer comprises a plurality of metallic nanostructures immobilized to the surface. Metallic nanostructures can be immobilized to the surface by treating the surface material with a reagent to add functional chemical groups, such as cyanide, amine, thiols, carboxyl, aldehyde or maleimide, and reacting the metallic nanostructures with the treated surface. Metallic nanostructures are known to bind to such functional chemical groups with high affinity. In some embodiments, the metallic nanostructures comprising the metallic nanolayer are spherical nanoparticles. Such nanoparticles have diameters that are less than about 300 nm, less than about 200 nm, or less than about 150 nm. In some embodiments, the spherical nanoparticles have a diameter from about 5 nm to about 200 nm, from about 10 nm to about 100 nm, or from about 20 nm to about 60 nm. In certain embodiments, the size of the metallic nanostructures used to create the metallic nanolayer are similar to the size of the composite nanostructures used in the detection conjugates. In such embodiments, matching the size of the two sets of nanostructures can provide an optimal wavelength shift in a reflectance, emission or scattering spectrum.

The metallic nanolayer (metallic film or plurality of metallic nanostructures) may be composed of a noble metal or composite thereof. In other embodiments, the metallic nanolayer (metallic film or plurality of metallic nanostructures) may be composed of a transition metal or composite thereof. In certain embodiments, the metallic nanolayer comprises a metal selected from gold, silver, copper, platinum, palladium, ruthenium, rhodium, osmium, iridium, titanium, chromium, cadmium, zinc, iron, cobalt, nickel, and composites thereof. In one particular embodiment, the metallic nanolayer (e.g. metallic film or plurality of metallic nanostructures) comprises gold. In another particular embodiment, the metallic nanolayer (e.g. metallic film or plurality of metallic nanostructures) comprises silver. In certain embodiments, the metallic nanolayer (e.g. metallic film or plurality of metallic nanostructures) comprises a composite of gold and silver or gold and copper. Use of alkali metals (e.g., lithium, sodium, potassium, rubidium, cesium, and francium) or lanthanides (e.g., lanthanum, cerium, praseodymium, neodymium, promethium, samarium, europium, gadolinium, terbium, dysprosium, holmium, erbium, thulium, ytterbium, and lutetium) may improve intensity of the LSPR peaks. Accordingly, in some embodiments, the metallic nanolayer (metallic film or plurality of metallic nanostructures) may be composed of one or more alkali metals or lanthanides. In other embodiments, the metallic nanolayer (metallic film or plurality of metallic nanostructures) may be composed of a combination of a noble metal and an alkali metal or lanthanide.

The analyte detection devices of the invention further comprise a plurality of capture molecules immobilized to the metallic nanolayer deposited on a surface. The capture molecules are capable of specifically binding to a target analyte. As used herein, "specific binding" refers to binding to a target molecule with high affinity, e.g., an affinity of at least $10^{-6}$M. In some embodiments, the capture molecules are haptens and other small molecules, drugs, hormones, biological macromolecules including, but not limited to, antibodies or fragments thereof (e.g., Fv, Fab, $(Fab)_2$, single chain, CDR etc.), antigens, receptors, ligands, polynucleotides, aptamers, polypeptides, polysaccharides, lipopolysaccharides, glycopeptides, lipoproteins, or nucleoproteins. In certain embodiments, the plurality of capture molecules are antibodies. In other embodiments, the plurality of capture molecules are antigens.

Methods of immobilizing molecules to metallic nanolayers or nanostructures are known to those of skill in the art. Such methods include conjugation chemistries, such as those involving 1-Ethyl-3-[3-dimethylaminopropyl]carbodiimide hydrochloride (EDC), sulfo-NHS coupling, hydrophobic binding or thioether chemistry. In some embodiments, the molecule can be coupled to the metallic nanolayer or nanostructure indirectly through a larger carrier molecule or protein. Such indirect coupling is particularly useful when the molecule is small, such as a hormone, a drug, and other small molecules less than 10 kD. Preferably, the carrier protein is not capable of specific interaction with the target analyte.

The analyte detection devices of the invention may also comprise a plurality of detection conjugates. Detection conjugates comprise metallic nanostructures coupled to binding partners capable of specifically binding to a target analyte or the capture molecules depending on the assay configuration. For example, in embodiments in which the device is configured in a sandwich assay format, the detection conjugates comprise metallic nanostructures coupled or conjugated to binding partners that are capable of specifically binding a target analyte. In other embodiments in which the device is configured in a direct competitive assay format, the detection conjugates comprise metallic nanostructures coupled or conjugated to target analytes.

The binding partners can be the same types of molecules as the capture molecules, including, but not limited to haptens and other small molecules, drugs, hormones, biological macromolecules such as antibodies or fragments thereof (e.g., Fv, Fab, $(Fab)_2$, single chain, CDR etc.), antigens, receptors, ligands, polynucleotides, aptamers, polypeptides, polysaccharides, lipopolysaccharides, glycopeptides, lipoproteins, or nucleoproteins. In some embodiments, the binding partners are the same type of molecule as the capture molecules, but preferably bind to the target analyte at a location distinct from the binding site of the capture molecules. By way of example, the binding partners and the capture molecules can both be antibodies that recognize a target analyte, but the epitope to which the binding partners bind the target analyte is separate from and ideally non-overlapping with the epitope to which the capture molecules bind the target analyte. Thus, in certain embodiments, the binding partners are antibodies that recognize a first epitope of a target analyte and the capture molecules are different antibodies that recognize a second epitope of a target analyte.

The metallic nanostructures in the detection conjugates can be composed of a noble metal or composite thereof. In some embodiments, the metallic nanostructures in the detection conjugates may be composed of a transition metal or composite thereof. In some embodiments, the metallic nanostructures in the detection conjugates may comprise an alkali metal or lanthanide in combination with a noble or transition metal. In certain embodiments, metallic nanostructures in the detection conjugates comprise a metal selected from gold, silver, copper, platinum, palladium, ruthenium, rhodium, osmium, iridium, titanium, chromium, cadmium, zinc, iron, cobalt, nickel, and composites thereof. In one embodiment, the metallic nanostructures are gold nanostructures. In another embodiment, the metallic nanostructures are silver nanostructures.

In preferred embodiments, the metallic nanostructures in the detection conjugates are composite metallic nanostructures. "Composite metallic nanostructures" refers to nanostructures that comprise at least two noble metals, transition metals, alkali metals, or lanthanides. The two or more metals may be mixed together, as in an alloy, or the two or more metals may be present in separate portions of the nanostructure. For example, one metal may form the core of the nanostructure, whereas the second metal forms an outer shell or coating of the nanostructure. In some embodiments, the composite metallic nanostructures comprise at least two metals selected from gold, silver, copper, platinum, palladium, ruthenium, rhodium, osmium, iridium, titanium, chromium, cadmium, zinc, iron, cobalt, and nickel. In other embodiments, the composite metallic nanostructures comprise at least two metals selected from gold, silver, copper, platinum, palladium, cadmium, iron, nickel, and zinc. In one particular embodiment, the composite metallic nanostructures comprise gold and silver. In another embodiment, the composite metallic nanostructures comprise gold and copper. In yet another embodiment, the composite metallic nanostructures comprise silver and copper.

In some embodiments, each of the composite metallic nanostructures is an alloy of a first metal and a second metal. In certain embodiments, each of the composite metallic nanostructures comprises a core of a first metal and a coating of a second metal. In one embodiment, the core is silver and the coating is gold. In another embodiment, the core is copper and the coating is gold. In another embodiment, the core is silver and the coating is copper. In some embodiments, each of the composite metallic nanostructures comprises a dielectric core (e.g. silicon dioxide, gold sulfide, titanium dioxide, silica, and polystyrene), a first coating of a first metal, and a second coating of a second metal. In one particular embodiment, the core is silica, the first coating (i.e. inner coating) is a silver coating, and the second coating is a gold coating (i.e. outer coating). In another embodiment, the core is silica, the first coating (i.e. inner coating) is a copper coating, and the second coating is a gold coating (i.e. outer coating).

In some embodiments, the core comprising a first metal is dissolved following the coating process with a second metal to create a hollow structure comprised of the second metal. For instance, coating of a silver core with gold nanoparticles generates a gold shell around the silver core and the silver core is subsequently dissolved or degraded resulting in the formation of a hollow nanogold shell structure.

The metallic nanostructures include spherical nanoparticles as well nanoplates and nanoshells. Nanoplates have lateral dimensions (e.g. edge lengths) that are greater than their thickness. Nanoplates include nanodisks, nanopolygons, nanohexagons, nanocubes, nanorings, nanostars, and nanoprisms. In some embodiments, the metallic nanostructures, including the composite nanostructures, have a geometry selected from spherical nanoparticles, pyramidal nanoparticles, hexagonal nanoparticles, nanotubes, nanoshells, nanorods, nanodots, nanoislands, nanowires, nanodisks, nanocubes, or combinations thereof. Other shapes are also possible, including irregular shapes. In certain embodiments, the size and shape of the metallic nanostructures are not uniform—i.e. the metallic nanostructures are a heterogeneous mixture of different shapes and sizes of nanostructures.

For spherical nanoparticles, suitable diameter ranges include from about 5 nm to about 200 nm, from about 10 nm to about 100 nm, and from about 20 nm to about 60 nm. For nanoplates, edge lengths may be from about 10 nm to about 800 nm, from about 20 nm to about 500 nm, from about to 50 nm to about 200 nm, from about 30 nm to about 100 nm, or from about 10 nm to about 300 nm. The thickness of the nanoplates can range from about 1 to about 100 nm, from about 5 nm to about 80 nm, from about 10 nm to about 50 nm, or from about 5 nm to about 20 nm.

In some embodiments, the nanoplates have an aspect ratio greater than 2. The aspect ratio is the ratio of the edge length to the thickness. Preferably, the nanoplates have an aspect ratio from about 2 to about 25, from about 3 to about 20, from about 5 to about 10, from about 2 to about 15, or from about 10 to about 30.

The binding partners or target analytes can be coupled or conjugated to the metallic nanostructures (e.g. composite nanostructures) using similar methods as described above for the immobilization of the capture molecules to the metallic nanolayer. Such methods include, but are not limited to, EDC conjugation chemistry, sulfo-NHS coupling, hydrophobic binding or thioether chemistry. The binding partners or target analytes can be coupled to the metallic nanostructures through various chemical functionalities including thiol, amine, dithiol, acrylic phosphoramidite, azide, or alkynes.

In some embodiments, the metal or metals employed in the metallic nanolayer deposited on the surface can be the same as the metal or metals from which the metallic nanostructures in the detection conjugates are fabricated. For example, in one embodiment, the metallic nanolayer deposited on the surface comprises a gold film or a plurality of gold nanostructures and the detection conjugates comprise gold nanostructures. In other embodiments, the metal employed in the metallic nanolayer deposited on the surface is different from the metal or metals used to create the metallic nanostructures in the detection conjugates. For instance, in some embodiments, the metallic nanolayer deposited on the surface comprises a silver film or a plurality of silver nanostructures and the detection conjugates comprise gold nanostructures. In other embodiments, the metallic nanolayer deposited on the surface comprises a gold film or a plurality of gold nanostructures and the detection conjugates comprise silver nanostructures. In certain embodiments, the metallic nanolayer deposited on the surface comprises a gold film or a plurality of gold nanostructures and the detection conjugates comprise composite nanostructures. In related embodiments, the composite nanostructures comprise gold-coated silver nanostructures. In other particular embodiments, the metallic nanolayer deposited on the surface comprises a gold film or a plurality of gold nanostructures and the detection conjugates comprise composite nanostructures comprising gold-coated copper nanostructures. In yet other embodiments, the metallic nanolayer deposited on the surface comprises a gold film or a plurality of gold nanostructures and the detection conjugates comprise composite nanostructures comprising gold-coated magnetite nanostructures. In still other embodiments, the metallic nanolayer deposited on the surface comprises a gold film or a plurality of gold nanostructures and the detection conjugates comprise composite nanostructures comprising gold and an alkali metal or lanthanide.

The present invention also includes kits comprising the analyte detection devices of the invention as disclosed herein. In one embodiment, the kit comprises (i) a surface containing a metallic nanolayer on which a plurality of capture molecules are immobilized and (ii) a composition comprising a plurality of detection conjugates as described herein. In certain embodiments, the composition is packaged separately from the surface such that it can be brought into subsequent contact with the surface during performance of the detection methods. In some embodiments, the composition comprising the plurality of detection conjugates is lyophilized, for example, in the form of a pellet or bead. In related embodiments, the surface containing the metallic nanolayer can be a chip, disc, or a cuvette. In one particular embodiment, the surface containing the metallic nanolayer is a cuvette adapted for use with a centrifugal rotor. In such embodiments, the metallic nanolayer may be deposited on the cover, bottom and/or walls of the cuvette.

In certain embodiments, all components of the analyte detection systems described herein are contained within a centrifugal rotor or disc. For instance, a rotor or disc may contain one or more reaction chambers in which the metallic nanolayer surface containing immobilized capture molecules and the plurality of detection conjugates are positioned. In one embodiment, the metallic nanolayer surface is a chip located at the bottom of the reaction chamber. In another embodiment, the metallic nanolayer is deposited directly on the floor of the reaction chamber. In still another embodiment, the metallic nanolayer surface is a bead (e.g. plastic bead) coated with the metallic nanolayer. In all such embodiments, the capture molecules are immobilized to the metallic nanolayer surfaces. In related embodiments, the plurality of detection conjugates is present in the form of a lyophilized composition, such as a lyophilized bead or pellet.

In alternative embodiments, capture molecules are conjugated to metallic nanostructures, which are in colloidal suspension. The plurality of detection conjugates is added to the suspension in the presence of a test sample. If the target analyte is present in the sample, complex formation will occur between the detection conjugates and the suspended nanostructures containing the capture molecules resulting in a change in optical signal (e.g., shift in peak absorbance wavelength of the suspended nanostructures).

Accordingly, in some embodiments, the kits comprise a rotor or disc having one or more reaction chambers, wherein each reaction chamber comprises (i) a lyophilized composition comprising a plurality of detection conjugates as described herein and (ii) a bead coated with a metallic nanolayer, wherein a plurality of capture molecules are immobilized to the metallic nanolayer. Such kits provide a one-step analyte detection assay whereby a test sample is contacted with the rotor or disc, and application of a centrifugal force to the rotor or disc delivers the test sample to the reaction chambers where the sample mixes with the plurality of detection conjugates and the metallic nanolayer-coated bead containing immobilized capture molecules. In embodiments in which the rotor or disc contains more than one reaction chamber, the detection conjugates and capture molecules can be selected such that a different analyte can be detected in each reaction chamber. These rotor-format detection devices can be configured in the sandwich assay format, the direct competitive format, or both if the rotors comprise multiple reaction chambers.

Any of the types of metallic nanolayers or metallic nanostructures discussed herein can be used with these rotor-format detection devices. In some embodiments, the metallic nanolayer coating on the bead is a gold nanolayer and the metallic nanostructures in the detection conjugates are gold nanostructures. In other embodiments, the metallic nanolayer coating on the bead is a silver nanolayer and the metallic nanostructures in the detection conjugates are gold nanostructures. In still other embodiments, the metallic nanolayer coating on the bead is a gold nanolayer and the metallic nanostructures in the detection conjugates are silver nanostructures. In one embodiment, the metallic nanolayer coating on the bead is a silver nanolayer overlaid with a gold nanolayer and the metallic nanostructures in the detection conjugates are gold nanostructures. In certain embodiments, the metallic nanolayer coating on the bead is a gold nanolayer and the metallic nanostructures in the detection conjugates are composite nanostructures. For instance, in one embodiment, the composite nanostructures are gold-coated silver nanostructures. In another embodiment, the composite nanostructures are gold-coated copper nanostructures.

The kits of the invention may also include instructions for using the device to detect an analyte in a test sample, devices or tools for collecting biological samples, and/or extraction buffers for obtaining samples from solid materials, such as soil, food, and biological tissues.

The present invention also provides methods of detecting a target analyte in a sample. In one embodiment, the methods comprise (i) mixing a test sample with a plurality of detection conjugates as described herein; (ii) contacting the mixture with a surface containing a metallic nanolayer, wherein a plurality of capture molecules as described herein are immobilized to the metallic nanolayer; (iii) exposing the surface to a light source at a wavelength range within the ultraviolet-visible-infrared spectrum; and (iv) measuring an optical signal from the surface, wherein a change in the optical signal indicates the presence of the target analyte in the sample.

In some embodiments, the detection methods are sandwich assays. In such embodiments, the detection conjugates comprise metallic nanostructures coupled to binding partners that are capable of specifically binding to the target analyte if present in the sample to form analyte-detection conjugate complexes. The plurality of capture molecules, which are immobilized to the metallic nanolayer surface, are also capable of specifically binding to the target analyte if present in the sample. The metallic nanolayer is exposed to a light source and an optical signal is measured, wherein a change in the optical signal indicates the presence of analyte in the sample. By way of illustration, when a sample containing the target analyte is mixed with the plurality of detection conjugates, the target analyte binds to the binding partners in the detection conjugates to form analyte-detection conjugate complexes. These complexes in turn bind to the plurality of capture molecules immobilized to the metallic nanolayer surface through the analyte thereby bringing the metallic nanostructures in the detection conjugates in close proximity to the metallic nanolayer surface. The amount of light that is absorbed or scattered by the metallic nanolayer surface is affected by the proximity of the metallic nanostructures in the complex and thus produces an enhanced shift in the peak absorption wavelength, which indicates the presence of the target analyte in the sample.

In other embodiments, the detection methods are competitive assays. In such embodiments, the detection conjugates comprise metallic nanostructures coupled to the target analyte of interest. As in the sandwich assay method, the plurality of capture molecules, which are immobilized to the metallic nanolayer surface, are capable of specifically binding to the target analyte. In this type of assay, the detection conjugates will bind to the capture molecules initially. If a sample containing a target analyte is mixed with these initial complexes, the unlabeled or free target analyte in the sample will compete with the detection conjugates for binding to the capture molecules. The change in optical signal in this type of assay will result from the displacement of the metallic nanostructures in the detection conjugates from the metallic nanolayer surface, which will proportionately reduce the wavelength shift in the peak absorption wavelength A test sample can be any type of liquid sample, including biological samples or extracts prepared from environmental or food samples. In one particular embodiment, the test sample is a biological sample. Biological samples include, but are not limited to, whole blood, plasma, serum, saliva, urine, pleural effusion, sweat, bile, cerebrospinal fluid, fecal material, vaginal fluids, sperm, ocular lens fluid, mucous, synovial fluid, peritoneal fluid, amniotic fluid, biopsy tissues, saliva, and cellular lysates. The biological sample can be obtained from a human subject or animal subject suspected of having a disease condition, such as cancer, infectious diseases (e.g., viral-, bacterial-, parasitic- or fungal-infections), cardiovascular disease, metabolic disease, autoimmune disease etc. The biological sample can also be obtained from a healthy subject (e.g. human or animal) undergoing a routine medical check-up.

In some embodiments of the methods, the test sample is mixed with the plurality of detection conjugates and the mixture is subsequently brought into contact with the metallic nanolayer surface containing the immobilized capture molecules. In other embodiments, the test sample is contacted with the metallic nanolayer surface containing the immobilized capture molecules and the plurality of detection conjugates is subsequently added. In certain embodiments, the sample, the plurality of detection conjugates, and the metallic nanolayer surface containing the immobilized capture molecules are brought into contact at the same time. For instance, contact of the sample with both reagents simultaneously may occur in the rotor-format detection devices described above.

Any of the analyte detection devices described above can be used in the detection methods of the present invention. Accordingly, the various metallic nanolayer surfaces, capture molecules, and detection conjugates described herein are suitable for use in the detection methods. For instance, in some embodiments of the methods, the surface containing a metallic nanolayer is a chip, a well, a cuvette, or a bead. In certain embodiments of the methods, the surface containing a metallic nanolayer is the walls and bottom of a cuvette incorporated into or adapted for use with a centrifugal rotor. In these and other embodiments, the metallic nanolayer on the surface is a metallic film, such as a gold film. In other embodiments of the methods, the metallic nanolayer on the surface comprises a plurality of metallic nanostructures immobilized on the surface, such as gold nanostructures.

In certain embodiments of the detection methods, the detection conjugates comprise composite metallic nanostructures coupled to binding partners or target analytes. As described herein, composite metallic nanostructures comprise at least two noble metals or transition metals. In some embodiments of the methods, the composite metallic nanostructures comprise at least two metals selected from gold, silver, copper, platinum, palladium, ruthenium, rhodium, osmium, iridium, titanium, chromium, cadmium, zinc, iron, cobalt, and nickel. In other embodiments of the methods, the composite metallic nanostructures comprise at least two metals selected from gold, silver, copper, platinum, palladium, cadmium, iron, nickel, and zinc. In one particular embodiment, the composite metallic nanostructures comprise gold and silver. In another embodiment, the composite metallic nanostructures comprise gold and copper. In yet another embodiment, the composite metallic nanostructures comprise silver and copper. The composite metallic nanostructures used in the methods of the invention can include a number of different geometries, such as spherical nanoparticles, pyramidal nanoparticles, hexagonal nanoparticles, nanotubes, nanoshells, nanorods, nanodots, nanoislands, nanowires, nanodisks, nanocubes, or combinations thereof.

In certain embodiments, the composite metallic nanostructures used in the methods of the invention are alloys of a first metal and a second metal. In some embodiments, the composite metallic nanostructures used in the methods of the invention comprise a core of a first metal and a coating of a second metal. In particular embodiments, the composite metallic nanostructures comprise a silver core and a gold coating. In other embodiments, the composite metallic nanostructures comprise a copper core and a gold coating. In another embodiment, the core is silver and the coating is copper. In some embodiments, each of the composite metallic nanostructures comprises a dielectric core (e.g. silicon dioxide, gold sulfide, titanium dioxide, silica, and polystyrene), a first coating of a first metal, and a second coating of a second metal. In one particular embodiment of the detection methods, the core is silica, the first coating (i.e. inner coating) is a silver coating, and the second coating is a gold coating (i.e. outer coating). In another embodiment, the core is silica, the first coating (i.e. inner coating) is a copper coating, and the second coating is a gold coating (i.e. outer coating).

The detection methods of the invention may be used to determine qualitative or quantitative amounts of a target analyte. Such methods are particularly useful for determining the approximate amount of a target analyte in a sample, which can be used inter alia to diagnose certain medical conditions or evaluate the efficacy of a drug therapy. In one embodiment, the quantity of a target analyte can be determined by establishing a standard curve for the particular analyte by measuring changes in optical signals from the metallic nanolayer surface as described herein for samples with a known quantity of target analyte; determining the optical signal change for a test sample; and comparing the optical signal change for the test sample to the values obtained for the standard curve. In some embodiments, determining the quantity of a complex between a first reagent and a second reagent comprises comparing the absorbance ratio and/or reaction rate from a test sample to the absorbance ratio and/or reaction rate from one sample with a known quantity of complex, thereby determining the quantity of the complex in the test sample. The quantitative values obtained from test samples may be compared to pre-determined threshold values, wherein said pre-determined threshold values are indicative of either an abnormal or normal level of the target analyte.

The detection methods of the present invention provide a highly sensitive technique for detecting minute quantities of a target analyte in a sample. As demonstrated by the working examples, amplification of plasmon resonance-based signals from gold nanolayer surfaces can be achieved with gold nanostructure conjugates such that nanogram quantities of target analyte can be detected in a sample. Thus, in one embodiment of the methods, the presence of nanogram quantities of a target analyte is detected. The inventors have surprisingly found that significantly greater amplification of plasmon resonance-based signals from gold nanolayer surfaces can be achieved with composite metallic nanostructure conjugates. Use of gold-coated silver nanostructures conjugated to an analyte-specific antibody enabled the detection of pictogram quantities of the target analyte, which is a 1000-fold increase in sensitivity as compared to that obtained with gold nanostructure conjugates. See Example 3. Accordingly, in some embodiments of the methods, the presence of picogram quantities of the target analyte is detected. In other embodiments of the methods, the presence of femtogram quantities of the target analyte is detected. Greater sensitivities may be obtained by altering the composition and/or shape of the composite metallic nanostructures and/or metallic nanolayer surface.

When incident light is applied to metallic nanostructures, conduction band electrons in the metal oscillate collectively at the same frequency of the incident electromagnetic wave. As a result of these resonance oscillations, the nanostructures strongly absorb and scatter light at a specific wavelength range. For metallic nanostructures comprising noble or transition metals, this wavelength range is in the ultraviolet-visible-infrared spectrum depending on the particular composition of the nanostructures. Thus, light sources for applying electromagnetic energy suitable for use in the methods of the invention can include any source that may apply a wavelength range within the ultraviolet-visible spectrum or ultraviolet-visible-infrared spectrum, including arc lamps and lasers. In some embodiments, the light source may be equipped with a monochromator so that specific wavelengths of light may be applied to the metallic nanolayer surface.

The optical properties of the metallic nanolayers and nanostructures depend on their size, shape, and composition. For instance, solid gold nanoparticles have an absorption peak wavelength ($\lambda_{max}$) from about 515 nm to about 560 nm depending on particle size. Gold spherical nanoparticles having a 30 nm diameter maximally absorb at about 520 nm with $\lambda_{max}$ shifting to longer wavelengths as particle diameter increases. Silver and copper particles have a $\lambda_{max}$ in the ultra-violet/blue or red region (e.g., from about 350 nm to about 500 nm) with increasing particle diameter causing a shift in $\lambda_{max}$ to longer wavelengths. Metallic nanorods have a transverse $\lambda_{max1}$ and a longitudinal $\lambda_{max2}$. Alloys of different metals typically exhibit absorption peaks in an intermediate range between the absorption peaks of the comprising metals. For example, nanostructures comprising a 50/50 alloy of gold and silver exhibit a $\lambda_{max}$ of about 470 nm with increasing amounts of gold causing a shift in the absorption peak to longer wavelengths. The sensitivity of the LSPR signals to changes in the local medium refractive index can be modified by changing the shape or geometry of the nanostructures. For instance, nonspherical particles (e.g. nanoprisms, nanorods, nanoshells, etc.) have increased LSPR sensitivities as compared to spheres. In some embodiments, the optical properties (e.g. absorption/scattering at particular wavelengths) are tailored to a particular application by varying the size, shape, or composition of the metallic nanolayer deposited on the surface or the metallic nanostructures employed in the detection conjugates.

The interaction between the incident light and the metallic nanolayer surface can be monitored as reflected light or transmitted light. The amount of the incident light that is absorbed or scattered can be measured as an absorption spectrum in a reflection mode or the absorption spectrum in a transmission mode. In some embodiments, the optical signal measured from the metallic nanolayer can be an optical reflection, an absorbance spectrum, a scattering spectrum, and/or an emission spectrum.

The plasmon coupling between the metallic nanolayer and the metallic nanostructures in the detection conjugates resulting from complex formation between the binding partners, target analyte, and capture molecules produces a change in the localized surface plasmon resonance spectrum of the metallic nanolayer. For instance, such changes can include an increased optical extinction, an increased optical reflection, and/or increased scattering and/or emission signal. In some embodiments, the change in optical signal indicative of the presence of the target analyte in the sample includes a shift, increase or decrease in optical scattering or a combination of these features. In certain embodiments, the change in optical signal indicative of the presence of the target analyte in the sample is a spectral peak wavelength shift. In one embodiment, the wavelength shift in the optical spectral peak may be a red shift (e.g., a shift to a longer wavelength) within a 200 nm to 1200 nm spectral window. In another embodiment, the wavelength shift in the optical spectral peak may be a blue shift (e.g., a shift to a shorter wavelength) within a 200 nm to 1200 nm spectral window. The changes in optical signals can be measured at a particular time point following a set reaction period. Additionally or alternatively, changes in the optical signal over the reaction period (e.g. rate determinations) may be measured. Both types of measurements can be used for either qualitative or quantitative analysis of a target analyte.

Various means for measuring optical signals at different wavelengths and acquiring extinction, scattering, or emission spectra are known in the art. Any spectrophotometric or photometric instruments are suitable for use in the disclosed methods. Some non-limiting examples include plate readers, Cobas Fara analyzers, and Piccolo Xpress® and Vetscan analyzers (Abaxis, Inc., Union City, CA), optic fiber readers (e.g., LightPath™ S4 (LamdaGen, Menlo Park, CA)), SPR instruments (e.g., Biacore instruments available from GE Healthcare), centrifugal analyzers from Olympus, Hitachi etc.

The present invention also includes an assay complex comprising (i) a detection conjugate that comprises a composite metallic nanostructure coupled to a binding partner, (ii) a target analyte, and (iii) a metallic nanolayer-coated bead on which a capture molecule is immobilized, wherein the binding partner in the detection conjugate is bound to a first epitope on the target analyte and the capture molecule is bound to a second epitope on the target analyte, thereby forming a complex comprising the detection conjugate, target analyte, and the capture molecule. In some embodiments, the assay complex is contained within a cuvette adapted for use with a centrifugal rotor. In other embodiments, the assay complex is contained within a reaction chamber in a centrifugal rotor or disc.

The binding partner and capture molecule in the assay complex can be any type of molecule described above, including haptens and other small molecules, drugs, hormones, biological macromolecules such as antibodies or fragments thereof (e.g., Fv, Fab, $(Fab)_2$, single chain, CDR etc.), antigens, receptors, ligands, polynucleotides, aptamers, polypeptides, polysaccharides, lipopolysaccharides, glycopeptides, lipoproteins, or nucleoproteins. In one embodiment, the binding partner is an antibody and the capture molecule is a different antibody.

The metallic nanolayer and composite metallic nanostructures are described in detail above. In one embodiment, the metallic nanolayer coating the bead (e.g. plastic or glass bead) is a gold nanolayer. In another embodiment, the metallic nanolayer coating the bead is a silver nanolayer. The bead is preferably less than 0.5 cm, but greater than 0.1 mm. In certain embodiments, the composite metallic nanostructures are gold-coated silver nanostructures. In other embodiments, the composite metallic nanostructures are gold-coated copper nanostructures. In still other embodiments, the metallic nanostructures comprise gold doped with silver, copper ions or both of these ions.

Any type of target analyte can be detected using the methods, devices, and assay complexes of the present invention, particularly those that are significant in the diagnoses of diseases. A target analyte can include, but is not limited to, a protein, enzyme, antigen, antibody, peptide, nucleic acid (RNA, DNA, mRNA, miRNA), hormone, glycoprotein, polysaccharide, toxin, virus, virus particle, drug molecule, hapten, or chemical. In some embodiments, the target analyte is a marker or antigen associated with an infectious disease in humans and/or animals. In other embodiments, the target analyte is a marker or antigen associated with a particular physiological state or pathological condition.

In certain embodiments, the target analyte is a pathogenic antigen or antibody to a pathogenic antigen. For instance, the pathogenic antigen can be a viral antigen (e.g., feline leukemia virus, canine parvovirus, foot and mouth virus, influenza virus, hepatitis a, b, c virus, HIV virus, human papilloma virus, Epstein Barr virus, rabies virus, etc.), a bacterial antigen (e.g., *Ehrlichia, Borrelia, Anaplasma, Anthrax, Salmonella, Bacillus*, etc.), a fungal antigen, or parasitic antigen (e.g., canine heartworm, *Giardia lamblia, Plasmodium falciparum, African trypanosomiasis, Trypanosoma brucei*, etc.). In other embodiments, the target analyte is a disease-related antigen or antibody to a disease-related antigen. Disease-related antigens include, but are not limited to, cancer-related antigens or markers (e.g., PSA, AFP, CA125, CA15-3, CA19-9, CEA, NY-ESO-1, MUC1, GM3, GD2, ERBB2, etc.), cardiovascular disease-related antigens or markers (e.g., troponin, C-reactive protein, brain natriuretic peptide, CKMB, fatty acid binding protein, etc.,), metabolic-related antigens or markers (e.g., thyroid stimulating hormone, thyroxine, leptin, insulin), or autoimmune disease-related antigens or markers (e.g., auto-antibodies). In certain embodiments, the target analyte is an inflammatory antigen or marker (e.g., C-reactive protein, MRP14, MRP8, 25F9, etc.). In other embodiments, the target analyte is a pregnancy-related antigen or marker (e.g., a fetal antigen, human chorionic gonadotropin).

The present invention also provides a method for preparing composite metallic nanostructures. In one embodiment, the method comprises preparing a first solution comprising a mixture of a polymer and chloroauric acid, preparing a second solution comprising silver or copper nanostructures, and incubating the first solution with the second solution for a period of time, wherein the resulting mixture comprises gold-coated silver nanostructures or gold-coated copper nanostructures. The resulting mixture preferably has a peak absorbance of about 515 nm to about 670 nm, or about 520 nm to about 560 nm. In one embodiment, the resulting mixture has a peak absorbance of about 530 nm.

The polymer used in the preparation of the first solution can be any one of polyvinylpyrrolidone, polyvinyl alcohol, polyacrylate, polyethylene glycol, polyethyleneimine, polyaspartic acid, polyglutamic acid, various gums, gelatin or mixed polymers comprising any of the foregoing. In one particular embodiment, the polymer is polyvinylpyrrolidone. Different types of coated nanostructures can be obtained by varying the molecular weight of the polymer. Suitable molecular weight ranges of the polymer include from about 5,000 Daltons to about 150,000 Daltons, about 10,000 Daltons to about 100,000 Daltons, from about 20,000 Daltons to about 80,000 Daltons. In some embodiments, the polymer has a molecular weight less than 50,000 Daltons. In other embodiments, the polymer has a molecular weight less than 20,000 Daltons. In certain embodiments, the polymer has a molecular weight of about 10,000 Daltons.

The characteristics of the gold coating can be controlled by adjusting the concentration ratio of polymer to chloroauric acid. For instance, the concentration ratio of polymer to chloroauric acid is from about 100:1 to about 1:100, from about 2:1 to about 5:1, or from about 1.5:1 to about 8:1. In some embodiments, the concentration ratio of polymer to chloroauric acid is 1:1. Suitable concentrations of polymer include, but are not limited to, about 0.1% to about 20% wt/wet in water or ethanol. Suitable concentrations of chloroauric acid include, but are not limited to, about 0.001 M to about 1.0 M, about 0.010 M to about 0.500 M, and about 0.050 M to about 0.100 M.

The coating efficiency and thickness can also be affected by the pH and halide content of the coating solution (i.e. first solution). In certain embodiments, the pH of the solution is kept in a range from about 3 to about 14. The halide content of the solution is, in some embodiments, less than 150 mM. In other embodiments, the halide content of the solution is in the range of about 0 to about 50 mM.

Methods of preparing solutions of silver and copper nanostructures are known to those of skill in the art. For instance, the second solution comprising silver or copper nanostructures can be prepared by any of the methods described in U.S. Patent Publication No. 2012/0101007, U.S. Patent Publication No. 2014/0105982, or U.S. Patent Publication No. 2013/0230717, each of which is hereby incorporated by reference in its entirety. In one embodiment, the second solution comprising silver or copper nanostructures is prepared by mixing a silver or copper source with a reducing agent. A suitable silver source includes a silver salt, such as silver nitrate. Suitable copper sources include copper (II) sulfate, copper (II) chloride, copper (II) hydroxide and copper (II) nitrate, copper (II) acetate and copper (II) trifluoroacetate. Reducing agents that can be reacted with the silver or copper sources to form the nanostructures can include glucose, ascorbic acid, sodium borohydride, and alkaline solutions (e.g. pH greater than 7.5) of polymers such as PVP. In certain embodiments, the reducing agent is ascorbic acid. The desired shape and optical spectral peak of the silver nanostructures or copper nanostructures can be attained by adjusting the ratios or concentrations of reactants as known to those of ordinary skill in the art. By way of example only, high concentrations of the reducing agent can result in pentagonal- and bipyramidal-shaped nanostructures, whereas low concentrations of the reducing agent can result in elongated nanowires or tubes. Depending on the particular shapes of the nanostructures, the second solution comprising silver or copper nanostructures may have a peak absorbance from about 550 nm to about 1000 nm, from about 600 nm to about 700 nm, from about 630 nm to about 680 nm, from about 750 nm to about 850 nm, from about 900 nm to about 940 nm, from about 580 nm to about 620 nm, or from about 550 nm to about 750 nm. In certain embodiments, the second solution comprising silver nanostructures has a peak absorbance of about 600 nm (i.e. 595 nm to 605 nm, inclusive). In some embodiments, the second solution comprising copper nanostructures has a peak absorbance of about 585 nm (i.e. 580 nm to 590 nm, inclusive). In some embodiments the peak absorbance of a solution comprising copper nanostructures is greater (i.e. red-shifted)

than the peak absorbance of a solution comprising silver nanostructures of a similar size and shape.

In some embodiments, the incubation period of the first solution with second solution is at least 12 hours. In other embodiments, the incubation period of the first solution with second solution is greater than 24 hours, preferably greater than 48 hours, more preferably at least 72 hours. Changes in the peak absorbance of the reaction mixture can be monitored during the incubation period to adjust the incubation time accordingly. For example, shifts of the peak absorbance to shorter wavelengths, for instance in the 520 nm to 550 nm region, can indicate that the gold-coated nanostructures have stabilized. In certain embodiments, stability of the resulting nanostructures to sodium chloride (e.g., 0.25-1M) is used to indicate a proper coating of the nanostructures.

In certain embodiments, the present invention provides methods of synthesizing nanostructures having optical densities greater than about 50/mL. In one embodiment, the methods comprise mixing a polymer as described herein with chloroauric acid, stirring the mixture at a set temperature for a first period of time, adding ascorbic acid to the mixture, and incubating the mixture for a second period of time. The size and shape of the nanostructures is dictated by the concentration ratio of polymer to chloroauric acid and the temperature and time of incubation. The concentrations of polymer and chloroauric acid can be in the ranges described above. The temperature can be adjusted based on the size and shape of the nanostructures desired, but may be in the range of about 4° C. to about 100° C. Similarly, the incubation period (i.e. first period of time) can be adjusted based on the desired properties of the nanostructures, but may range from about 15 minutes to one day.

In some embodiments, about 0.1 to 1 part of ascorbic acid (e.g. about 1 to 5 M) is added to the mixture following the first incubation period. The second incubation period following addition of the ascorbic acid may be from about 1 to about 24 hours. Without being bound by theory, addition of ascorbic acid provides a substantial increase in the quantity of nanostructures produced.

In certain embodiments, the methods further comprise adding or doping the mixture with about 1 to about 100 parts of gold chloride (e.g. about 0.001 M to 1M) or silver nitrate (e.g. about 0.001 M to 1M) or other metal (e.g. noble metal, transition metal, alkali metal, or lanthanide). This doping step can further increase the resonance intensity of the resulting nanostructures. In some embodiments, the gold chloride, silver nitrate, or other metal is added to the mixture before ascorbic acid is added to the reaction. In other embodiments, the gold chloride, silver nitrate, or other metal is added to the mixture following the addition of ascorbic acid. The order of addition of the metal and ascorbic acid may be adjusted to tailor the resulting nanostructures to a desired shape and size.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

All patent and non-patent documents referenced throughout this disclosure are incorporated by reference herein in their entirety for all purposes.

EXAMPLES

Example 1. Amplification of LSPR Signals with Gold Nanoparticle-Conjugated Analyte An analyte detection system was prepared by providing a plastic chip on which was deposited a gold nanolayer film. Human IgG proteins (100 μg/ml) were immobilized to the gold nanolayer film to create the sensor surface. A control sensor was constructed by immobilizing bovine serum albumin to the gold nanolayer film. The two types of sensor surfaces were positioned within an instrument equipped with light emitting and light collecting fibers that shine light on the gold nanolayer surface and collect the light reflected back from the surface.

A sample containing free protein A (10 μg/ml) was contacted with the two types of sensor surfaces and the changes in the reflectance spectra were measured. As shown in FIG. 1, introduction of free protein A to the sensor containing immobilized human IgG does not produce a significant visible change in the reflectance spectrum of the gold nanolayer film as measured by a shift in the peak wavelength.

The sensor surfaces were regenerated by treatment with 1 mM hydrochloric acid and sample containing protein A conjugated to colloidal gold nanoparticles (CGC) at two different concentrations (3.5 μg/ml and 0.175 μg/ml) were contacted with the sensor surfaces. The change in the reflectance spectrum of the gold nanolayer surface was accentuated when the protein A (i.e. target analyte) was conjugated to colloidal gold nanoparticles. Specifically, 3.5 μg/ml of protein A-CGC produced a greater shift in peak wavelength than 10 μg/ml of unlabeled protein A. See FIG. 1, sensor 2. The amplification of the plasmon resonance signal was sufficiently great to enable detection of nanogram concentrations of protein A-CGC. See FIG. 1, sensor 3. The changes in the reflectance spectrum of the BSA sensor represent non-specific binding of the protein A molecules to the sensor surface and are significantly smaller than the changes induced by specific binding of the protein A molecules to the immobilized IgG molecules.

The results of this initial experiment show that considerable amplification of the changes in localized surface plasmon resonance signals induced by binding events at a metallic nanolayer surface can be achieved by coupling the target analyte to colloidal gold nanoparticles. Nearly a 60-fold improvement in sensitivity is observed with nanogram quantities of analyte being detected.

Example 2. Amplification of LSPR Signals in a Sandwich Assay

This example describes a series of experiments designed to evaluate whether amplification of localized surface plasmon resonance signals with gold nanoparticle conjugates could also be achieved in a sandwich assay format in which the target analyte is not directly conjugated to the gold nanoparticles. A gold nanolayer chip surface was prepared as described in Example 1. The C7 antibody against C-reactive protein (CRP) (100 μg/ml) was immobilized to the gold nanolayer film deposited on the chip surface to create the anti-CRP sensor. The C6 antibody, which recognizes a distinct, non-overlapping epitope of CRP than the C7 antibody, was conjugated to colloidal gold nanoparticles (C6-CGC) for some experiments or used in an unlabeled form for other experiments.

Figure 2:
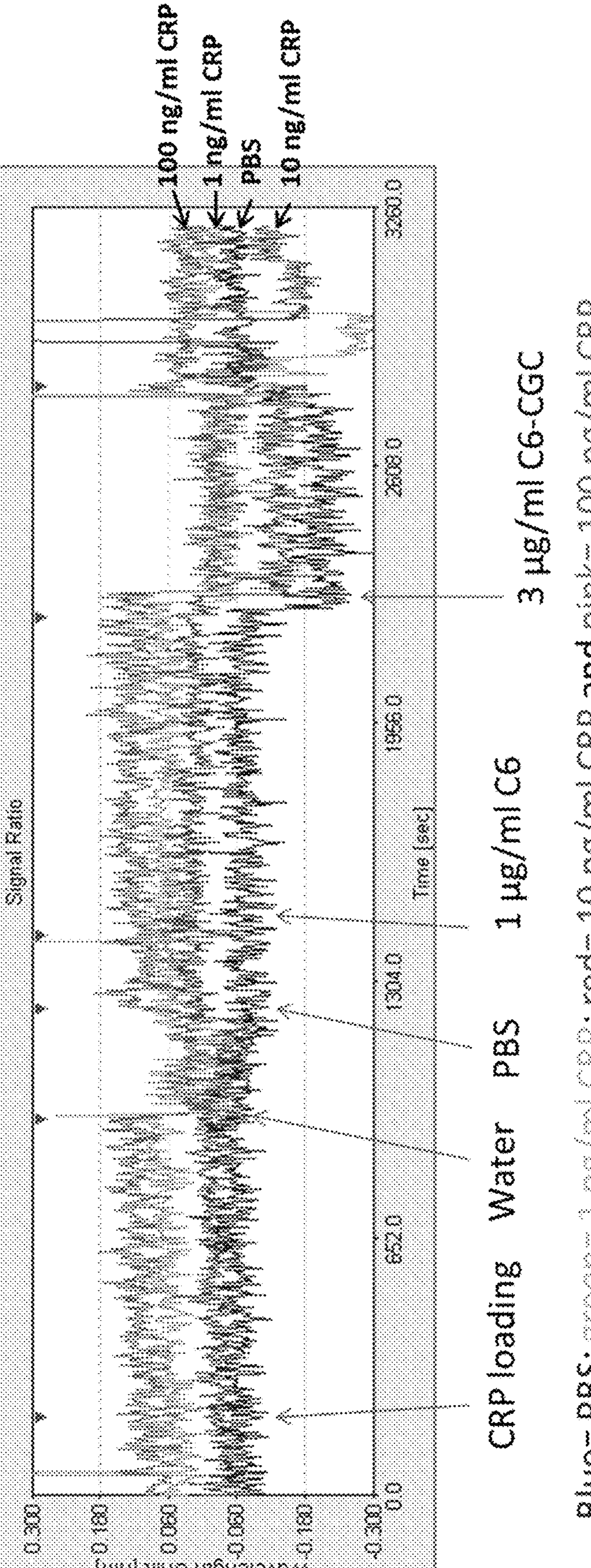
FIG. 2. Plot of shift in peak wavelength versus acquisition time for an anti-CRP C7 antibody-coupled gold nanolayer sensor. Arrows indicate injection sequence of 0 to 100 ng/ml concentrations of CRP in different channels (CRP loading), 1 μg/ml unlabeled anti-CRP C6 antibody, or 3 μg/ml anti-CRP C6 antibody labeled with colloidal gold (C6-CGC). No further C6-CGC binding was observed when sensor surface was occupied with unlabeled anti-CRP C6 antibody.

In a first series of experiments, a sample containing one of three different concentrations of CRP (1 ng/ml, 10 ng/ml, or 100 ng/ml) was incubated with the anti-CRP sensor for 15 to 20 minutes and changes in the reflectance spectrum of the gold nanolayer were monitored. As shown in FIG. 2, very minimum peak shift was observed upon binding of the CRP to the immobilized C7 anti-CRP antibody on the sensor surface. Subsequent exposure of the sensor surface to unlabeled C6 anti-CRP antibody (1 μg/ml) did not result in significant further peak shifts. See FIG. 2. Similarly, subsequent exposure of the sensor surface to 3 μg/ml of C6-CGC did not produce any further changes in the reflectance spectrum, indicating that the bound CRP molecules were likely saturated with unlabeled C6 antibody. See FIG. 2.

Figure 3:
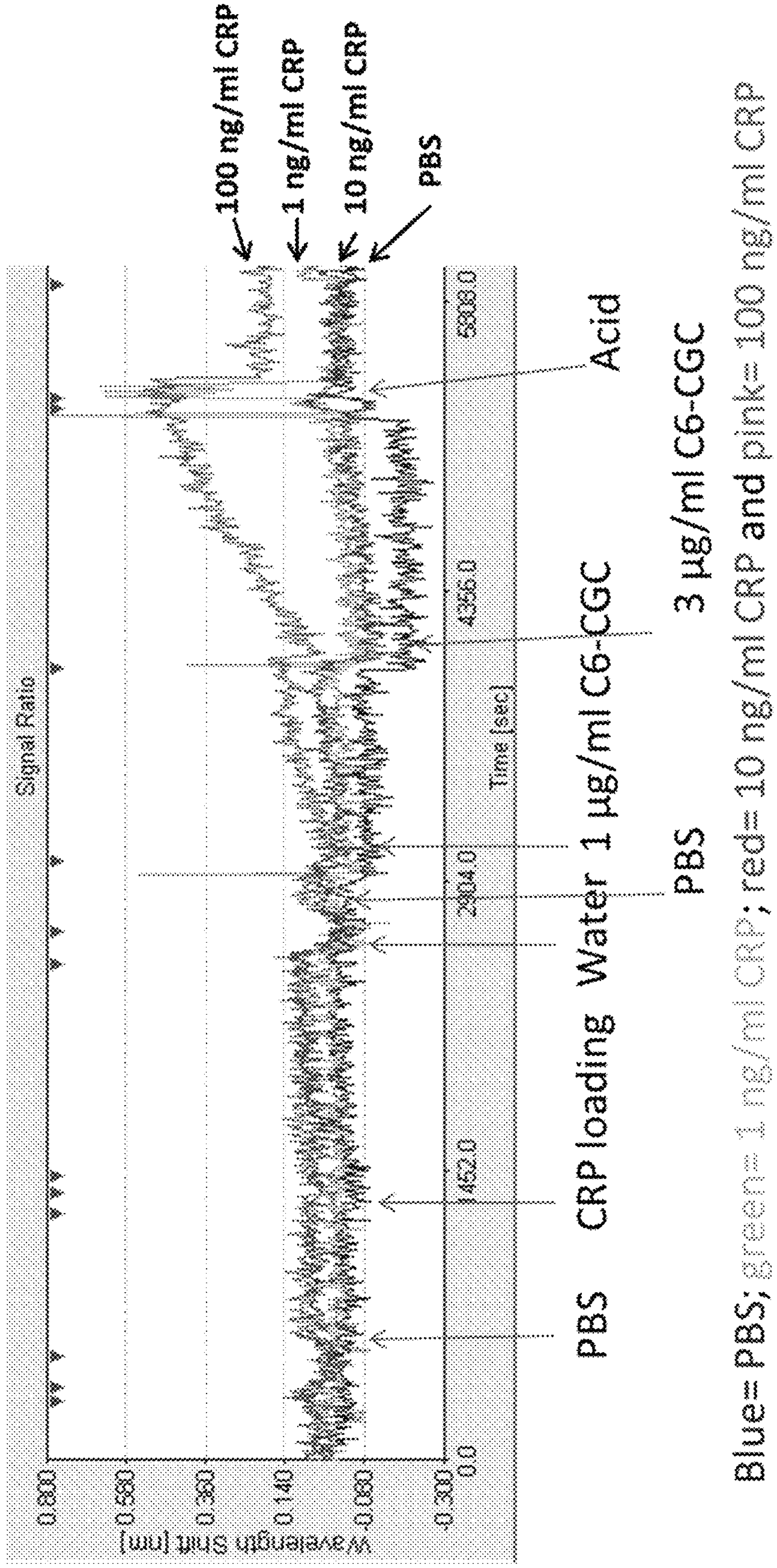
FIG. 3. Plot of shift in peak wavelength versus acquisition time for an anti-CRP C7 antibody-coupled gold nanolayer sensor. Arrows indicate the injection sequence of 0 to 100 ng/ml concentrations of CRP in different channels (CRP loading), 1 μg/ml anti-CRP C6 antibody labeled with colloidal gold (C6-CGC), 3 μg/ml C6-CGC, or 1 mM HCl (Acid).
Figure 4A:
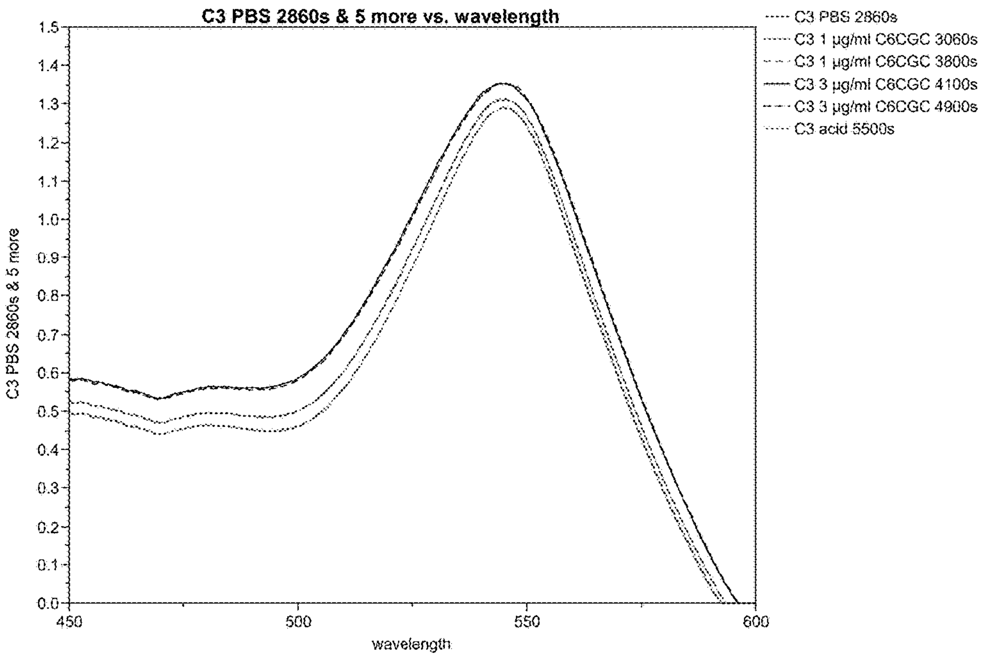
FIG. 4A (panel A). Reflectance spectra of anti-CRP C7 antibody-coupled gold nanolayer sensors loaded with 10 ng/ml CRP at the various C6-CGC concentrations in FIG. 3.
Figure 4B:
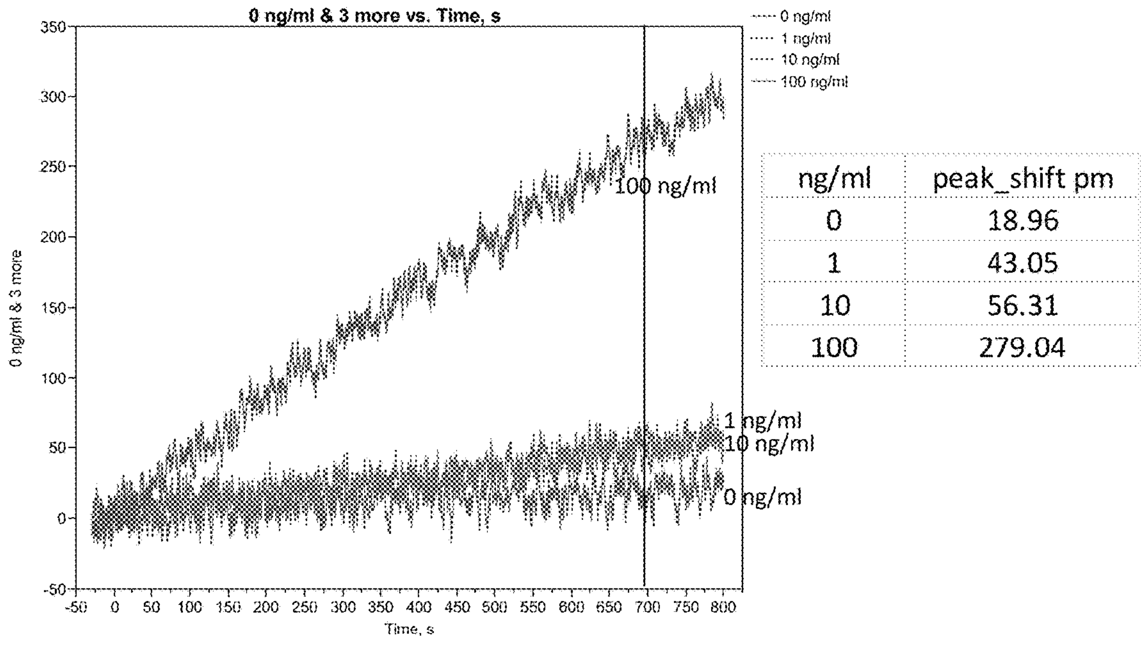
FIG. 4B (panel B). Plot of shift in peak wavelength versus acquisition time for an anti-CRP C7 antibody-coupled gold nanolayer sensor incubated with one of three concentrations of CRP following introduction of 3 μg/ml anti-CRP C6 antibody labeled with colloidal gold (C6-CGC). The table at the right depicts peak analysis 700 seconds after introduction of C6-CGC.

In a second series of experiments, a sample containing one of three different concentrations of CRP (1 ng/ml, 10 ng/ml, or 100 ng/ml) was incubated with the anti-CRP sensor for 15 to 20 minutes. Two different concentrations of C6-CGC (1 μg/ml and 3 μg/ml) were subsequently introduced and changes in the reflectance spectrum were measured (FIG. 3 and panel A of FIG. 4A). The results show that conjugation of the C6 anti-CRP antibody to gold nanoparticles amplifies the peak wavelength shift as compared to unlabeled C6 antibody. Increasing concentrations of C6-CGC produce a dose-dependent shift in peak wavelength. However, the signal difference between 1 ng/ml and 10 ng/ml was small (panel B of FIG. 4B).

Figure 5:
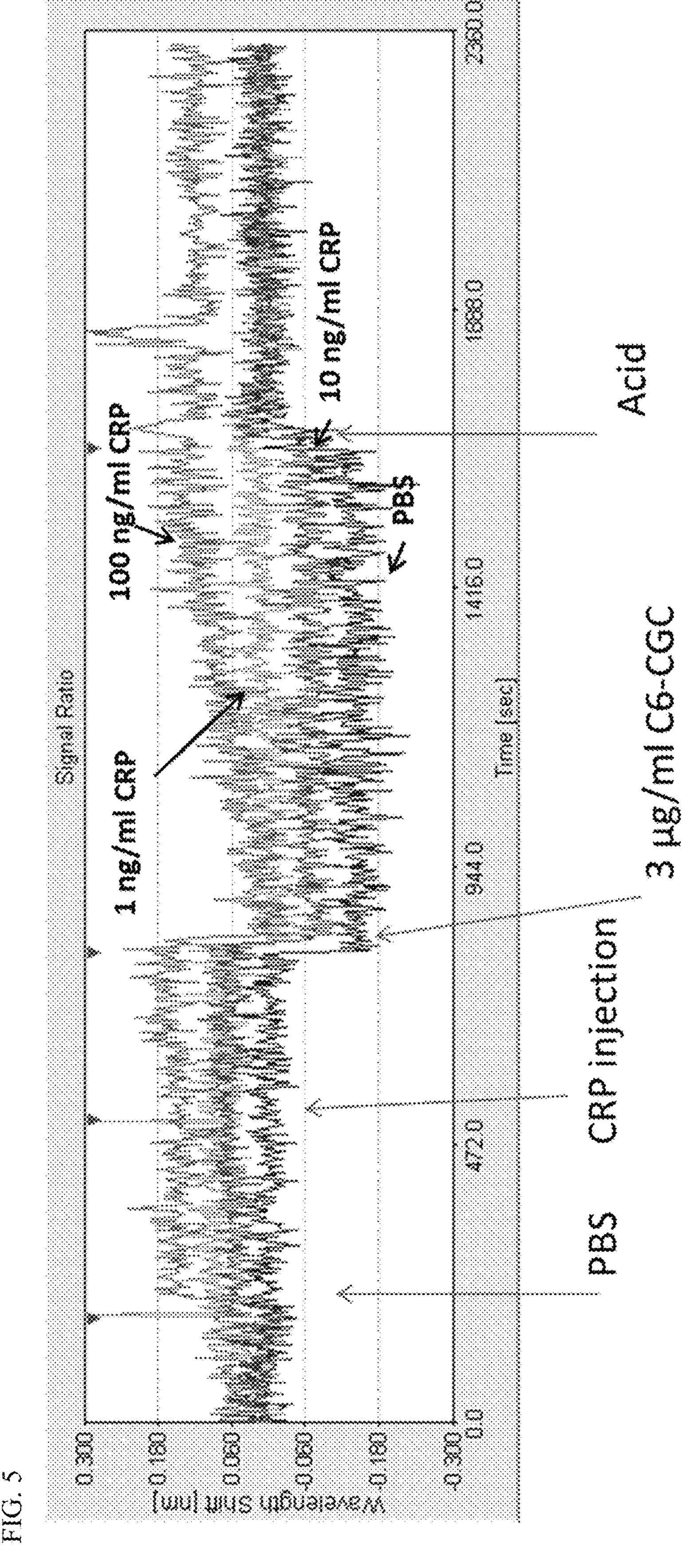
FIG. 5. Plot of shift in peak wavelength versus acquisition time for an anti-CRP C7 antibody-coupled gold nanolayer sensor. Arrows indicate the injection sequence of 0 to 100 ng/ml concentrations of CRP in different channels (CRP loading with incubation time minimized), 3 μg/ml anti-CRP C6 antibody labeled with colloidal gold (C6-CGC), or 1 mM HCl (Acid).
Figure 6:
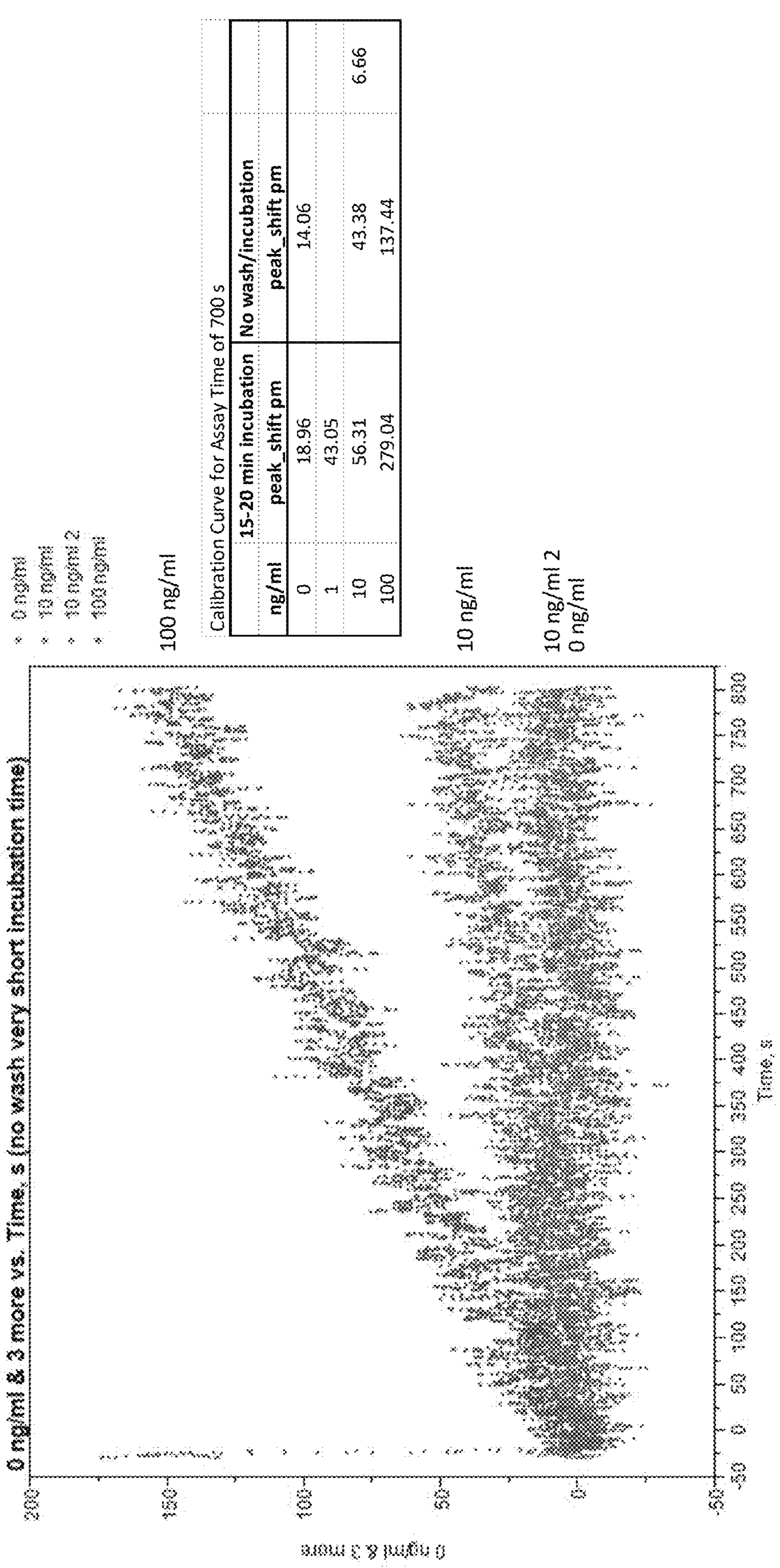
FIG. 6. Plot of shift in peak wavelength versus acquisition time for traces in FIG. 5 following immediate introduction of 3 μg/ml anti-CRP C6 antibody labeled with colloidal gold (C6-CGC). The table at the right depicts peak analysis 700 seconds after introduction of C6-CGC as compared to the peak shifts obtained with CRP incubation (values shown in panel B (bottom panel) of FIG. 4B).

In a third series of experiments, the effect of analyte incubation time on signal development was evaluated. The anti-CRP sensor was contacted with sample containing 0 ng/ml, 10 ng/ml, or 100 ng/ml CRP and 3 μg/ml C6-CGC was immediately introduced without any analyte incubation time or a wash. As shown in FIGS. 5 and 6, shorter analyte incubation time results in smaller peak wavelength shifts.

The results of these three sets of experiments show that amplification of LSPR signals can be achieved with gold nanoparticle conjugates in a sandwich assay format. An enhanced signal shift is observed when the detector antibody is labeled with colloidal gold particles as compared to unlabeled antibody, thereby allowing for detection of nanogram concentrations of analyte.

Example 3. Enhanced Signal Amplification with Gold-Coated Silver Nanostructures

To examine whether varying the type of metal used to label the binding partners affected the amplification of LSPR signals, composite metal nanostructures were prepared. Specifically, gold-coated silver nanostructures were prepared as follows. Silver nanostructures were prepared by adding 50.0 mL of deionized $H_2O$, 500.0 μL Trisodium Citrate (75 mM), 200 μL $AgNO_3$ (200 mM), and 500.0 μL $H_2O_2$ (27%) while stirring vigorously at room temperature. A 500 μL aliquot of $NaBH_4$ (200 mM) was then rapidly injected into the aqueous solution causing a color change to light yellow. Over a period of several minutes the color continued to change from dark yellow to red to purple and finally stabilizing at blue. The UV/Vis spectra determined the peak absorbance of the solution to be at 604.5 nm.

A gold coating was added to the silver nanostructures by adding 5.0 mL of the blue solution to a mixture of 50 μL of Polyvinylpyrrolidone (PVP MW≈10,000 20% in ethanol) and 50 μL of $HAuCl_4$ (20 mM). After 72 hours of incubation time the sample became a dark red color and had a peak absorbance at 534.5 nm. The nanoparticles were washed twice by centrifugation at 20,000 rpm for 20 minutes and resuspended in 2.0 mL of deionized $H_2O$. The solution had a deep red color, absorption peak at 530.3 nm, and a total absorbance of 15.0 OD units.

Conjugation of gold-coated silver nanostructures (Au@AgNPs) to the C6 anti-CRP antibody was performed by adding 600.0 μL of Au@AgNPs and 20.0 μL C6 anti-CRP antibody (8.0 mg/mL) to 880.0 μL deionized $H_2O$ bringing the final antibody concentration to 17.8 μg/mL/OD. After a 2 hour incubation period at 4° C., the sample was centrifuged at 30,000 g for 20 minutes and resuspended in 1.5 mL of a blocking solution containing BSA (10 mg/mL) in PBS. The Au@AgNPs conjugated to anti-CRP C6 antibody were stored at 4° C. until further use.

The anti-CRP gold nanolayer sensor was prepared as described in Example 2 and had peak absorption at 530 nm. A control sensor containing the gold nanolayer without any immobilized antibody was also prepared. The sensors were equilibrated with 100 μL PBS.

Figure 7:
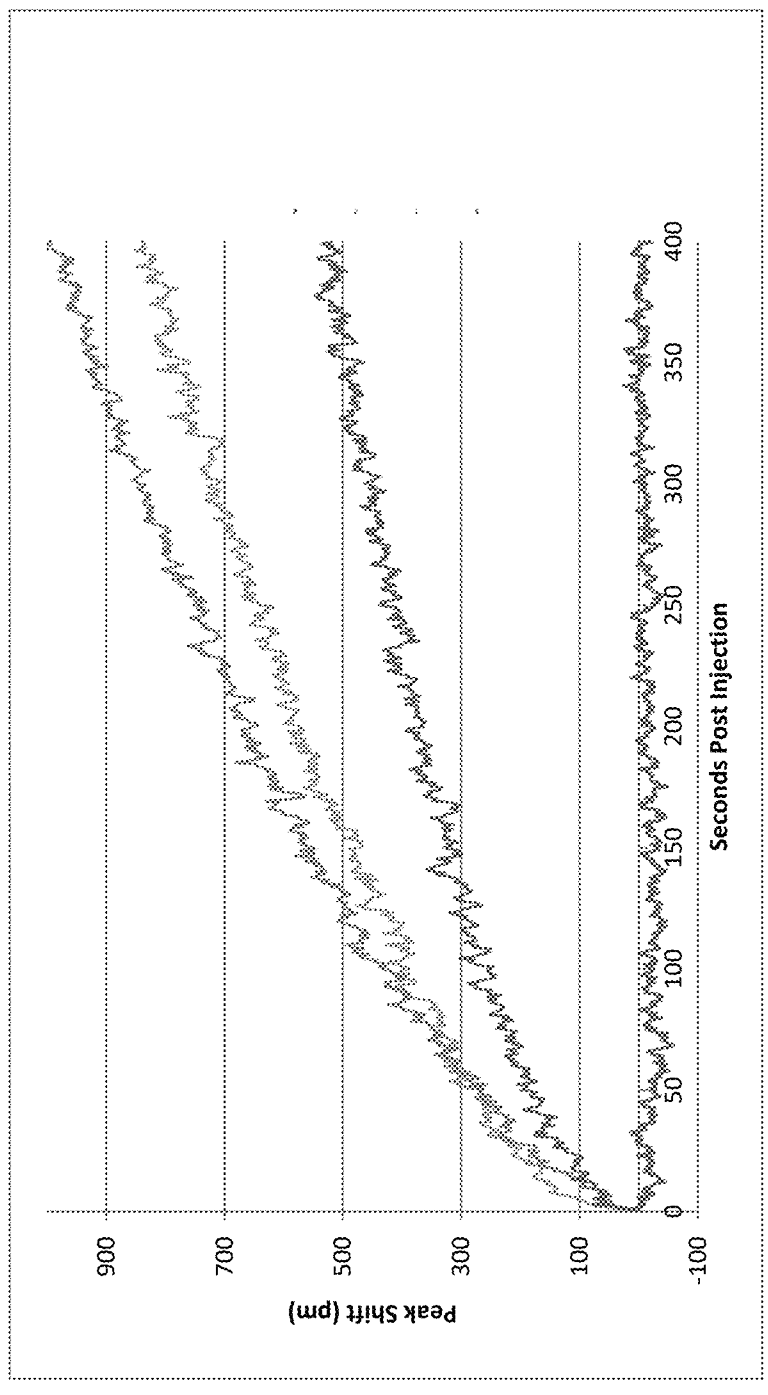
FIG. 7. Plot of shift in peak wavelength versus acquisition time for an anti-CRP C7 antibody-coupled gold nanolayer sensor incubated with one of three concentrations of CRP and C6 anti-CRP antibody conjugated to gold-coated silver nanostructures. The control was a gold nanolayer sensor with immobilized bovine serum albumin (BSA) in place of C7 antibody.

100 μL C6 anti-CRP antibody conjugated to Au@AgNPs diluted to 1.5 OD in PBS was premixed for 1 minute with 1, 10, or 500 pg/mL CRP antigen. The mixture was then brought into contact with the anti-CRP or control sensor surface and changes in the reflectance spectrum of the gold nanolayer surface were measured. The results show that the gold-coated silver nanostructures enhanced the peak wavelength shift induced by binding of the CRP-antibody complex to the sensor surface (FIG. 7). Detection of 1 pg/mL of CRP antigen was possible with the gold-coated silver nanostructures, which is a 1000-fold improvement in sensitivity as compared to that obtained with gold nanoparticles. At higher concentrations of antigen the binding sites are saturated and no further shifts occur.

The results of this experiment demonstrate the significantly enhanced amplification of LSPR signals from a metallic nanolayer surface achieved when composite nanostructures, such as gold-coated silver nanostructures, are used to label analyte binding partners.

Example 4. Synthesis of High Optical Density Nanostructures

Gold nanoparticles were prepared by mixing the following reagents in a final volume of 1 ml in the indicated order: 0.1 ml of 1% PVP-10 (1% wt/wt), 0.2 ml of 0.1M gold chloride, 0.1 ml of 5N NaOH, 0.4 ml of water and 0.2 ml of 1M ascorbic acid. The reaction mixture was mixed after each addition. The spectroscopic measurements indicated that the reaction was mostly complete after 24 hours at room temperature. This protocol yielded spherical gold nanoparticles exhibiting the LSPR peak around 535 nm and the corresponding optical density of about 80 per ml. Layering with additional gold or silver was done by adding silver nitrate or gold chloride to the preformed gold nanoparticles. Excess reagents were removed by centrifugation at 30,000 g for 1-2 hours.

In a separate reaction, 0.05 ml of 20% PVP (wt/wt) was mixed with 0.25 ml water, 0.1 ml of 5N NaOH, 0.1 ml of 1 M sodium citrate, 0.5 ml of 0.1M gold chloride and 1 ml of 1M ascorbic acid. This protocol resulted in immediate formation of colloidal gold particles at an OD of about 90/ml with LSPR peak at ~525 nm. A linear correspondence was observed between final OD and the concentration of gold between 2.5 mM gold and 25 mM gold in the final reaction mixture.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A localized surface plasmon resonance (LSPR) analyte detection device comprising:

a plurality of detection conjugates, wherein the conjugates comprise composite metallic nanostructures coupled to binding partners that are capable of specifically binding to a target analyte, wherein the composite metallic nanostructures comprise a silver core and a gold coating;

a surface containing a metallic nanolayer; and a plurality of capture molecules, wherein the capture molecules are immobilized on the metallic nanolayer and are capable of specifically binding to the target analyte.

2. A localized surface plasmon resonance (LSPR) analyte detection device comprising:

a plurality of detection conjugates, wherein the conjugates comprise composite metallic nanostructures coupled to target analytes, wherein the composite metallic nanostructures comprise a silver core and a gold coating;

a surface containing a metallic nanolayer; and a plurality of capture molecules, wherein the capture molecules are immobilized on the metallic nanolayer and are capable of specifically binding to the target analytes.

3. The LSPR analyte detection device of claim 1, wherein the composite metallic nanostructures are spherical nanoparticles and have a diameter of about 5 nm to about 200 nm.

4. The LSPR analyte detection device of claim 1, wherein the composite metallic nanostructures are spherical nanoparticles and have a diameter of about 10 nm to about 100 nm.

5. The LSPR analyte detection device of claim 1, wherein the composite metallic nanostructures are nanoplates with an edge length of about 10 nm to about 800 nm and a thickness of about 1 nm to about 100 nm.

6. The LSPR analyte detection device of claim 1, wherein the plurality of detection conjugates is in the form of a lyophilized pellet or bead.

7. The LSPR analyte detection device of claim 1, wherein the surface is a chip, a well, a bead, or a wall, cover, and/or bottom of a cuvette.

8. The LSPR analyte detection device of claim 1, wherein the metallic nanolayer is a metallic film.

9. The LSPR analyte detection device of claim 8, wherein the metallic film comprises gold, silver, copper, platinum, palladium, cadmium, zinc or a composite thereof.

10. The LSPR analyte detection device of claim 8, wherein the metallic film comprises gold.

11. The LSPR analyte detection device of claim 1, wherein the metallic nanolayer comprises a plurality of metallic nanostructures immobilized on the surface.

12. The LSPR analyte detection device of claim 11, wherein the plurality of metallic nanostructures comprise gold, silver, copper, platinum, palladium, cadmium, zinc or a composite thereof.

13. The LSPR analyte detection device of claim 11, wherein the plurality of metallic nanostructures are gold nanostructures.

14. The LSPR analyte detection device of claim 1, wherein the composite nanostructures have a geometry selected from spherical nanoparticles, pyramidal nanoparticles, hexagonal nanoparticles, nanoshells, nanotubes, nanorods, nanodots, nanoislands, nanowires, or combinations thereof.

15. The LSPR analyte detection device of claim 1, wherein the binding partners and/or capture molecules are antibodies, antigens, polypeptides, polynucleotides, nucleoproteins, aptamers, ligands, receptors, or haptens.

16. The LSPR analyte detection device of claim 1, wherein the binding partners are antibodies that recognize a first epitope of a target analyte and the capture molecules are different antibodies that recognize a second epitope of a target analyte.

17. The LSPR analyte detection device of claim 2, wherein the capture molecules are antibodies, antigens, polypeptides, polynucleotides, nucleoproteins, aptamers, ligands, receptors, or haptens.

18. The LSPR analyte detection device of claim 1, wherein the target analyte is a marker or antigen associated with an infectious disease, physiological state, or pathological condition.

19. The LSPR analyte detection device of claim 1, wherein the target analyte is canine heartworm, feline leukemia virus, canine parvovirus, C-reactive protein, *Giardia lamblia, Ehrlichia* antigen or antibody, *Borrelia* antigen or antibody, *Anaplasma* antigen or antibody, a cancer antigen, a cardiac marker antigen, thyroid stimulating hormone, thyroxine, troponin, or brain natriuretic peptide.

20. A method of detecting a target analyte in a sample based on localized surface plasmon resonance (LSPR), the method comprising:

mixing the sample with a plurality of detection conjugates, wherein the conjugates comprise composite metallic nanostructures coupled to binding partners that are capable of specifically binding to the target analyte if present in the sample to form analyte-detection conjugate complexes, wherein the composite metallic nanostructures comprise a silver core and a gold coating;

contacting the mixture with a surface containing a metallic nanolayer, wherein a plurality of capture molecules are immobilized on the metallic nanolayer and are capable of specifically binding to the target analyte if present in the sample;

exposing the surface to a light source at a wavelength range within the ultraviolet-visible-infrared spectrum; and measuring an optical signal from the surface, wherein a change in the optical signal indicates the presence of the target analyte in the sample.

21. The method of claim 20, wherein the optical signal is reflectance, an absorbance spectrum, scattering spectrum, or an emission spectrum.

22. The method of claim 20, wherein the change in the optical signal comprises a spectral peak wavelength shift.

23. The method of claim 20, wherein the presence of nanogram quantities of the target analyte is detected.

24. The method of claim 20, wherein the presence of picogram quantities of the target analyte is detected.

25. The method of claim 20, wherein the presence of femtogram quantities of the target analyte is detected.

26. The method of claim 20, wherein the surface is the walls and bottom of a cuvette incorporated into a centrifugal rotor.

27. The method of claim 20, wherein the metallic nanolayer is a metallic film.

28. The method of claim 27, wherein the metallic film comprises gold.

29. The method of claim 20, wherein the metallic nanolayer comprises a plurality of metallic nanostructures immobilized on the surface.

30. The method of claim 29, wherein the plurality of metallic nanostructures are gold nanostructures.

31. The method of claim 20, wherein the composite nanostructures have a geometry selected from spherical nanoparticles, pyramidal nanoparticles, hexagonal nanoparticles, nanotubes, nanoshells, nanorods, nanoislands, nanodots, nanowires, or combinations thereof.

* * * * *